!

US011572546B2

(12) United States Patent
Tsakraklides et al.

(10) Patent No.: US 11,572,546 B2
(45) Date of Patent: Feb. 7, 2023

(54) METHODS AND COMPOSITIONS INVOLVING PROMOTERS DERIVED FROM YARROWIA LIPOLYTICA

(71) Applicant: GINKGO BIOWORKS, INC., Boston, MA (US)

(72) Inventors: Vasiliki Tsakraklides, Lexington, MA (US); Annapurna Kamineni, Watertown, MA (US)

(73) Assignee: GINKGO BIOWORKS, INC., Boston, MA (US)

( * ) Notice: Subject to any disclaimer, the term of this patent is extended or adjusted under 35 U.S.C. 154(b) by 0 days.

(21) Appl. No.: 16/942,509

(22) Filed: Jul. 29, 2020

(65) Prior Publication Data
US 2021/0032604 A1 Feb. 4, 2021

Related U.S. Application Data

(60) Provisional application No. 62/879,989, filed on Jul. 29, 2019.

(51) Int. Cl.
*C12N 9/02* (2006.01)
*C12P 7/64* (2022.01)
*C12N 15/81* (2006.01)

(52) U.S. Cl.
CPC .......... *C12N 9/0071* (2013.01); *C12N 15/81* (2013.01); *C12P 7/64* (2013.01); *C12Y 114/19001* (2013.01); *C12Y 114/19006* (2013.01)

(58) Field of Classification Search
None
See application file for complete search history.

(56) References Cited

U.S. PATENT DOCUMENTS

| | | | |
|---|---|---|---|
| 4,683,202 | A | 7/1987 | Mullis |
| 7,238,482 | B2 | 7/2007 | Picataggio et al. |
| 7,259,255 | B2 | 8/2007 | Picataggio et al. |
| 7,264,949 | B2 | 9/2007 | Xue et al. |
| 2006/0094102 | A1 | 5/2006 | Xue et al. |
| 2009/0093543 | A1 | 4/2009 | Xue et al. |
| 2011/0059204 | A1 | 3/2011 | Jackson et al. |
| 2012/0289600 | A1 | 11/2012 | Xue et al. |

OTHER PUBLICATIONS

Zheng et al., The initial step of the glycerolipid pathway, J. Biol. Chem. 276, 2001, 41710-16. (Year: 2001).*
User Manual, pYES2, Cat. No. V824-20, Invitrogen, 2008. (Year: 2008).*
Fulmer et al., Studies on Yeast: VI. On the Continuous Growth of *Saccharomyces cerevisiae* in Synthetic Mediums, J. Infectious Diseases 33, 1923, 130-33. (Year: 1923).*
Kamineni et al., Promoters for lipogenesis-specific downregulation in Yarrowia lipolytica, FEMS Yeast Res. 20, 2020, foaa035. (Year: 2020).*
Hussain et al., Engineering Promoter Architecture in Oleaginous Yeast Yarrowia lipolytica, ACS Synth. Biol. 5, 2016, 213-23. (Year: 2016).*
Abghari et al., "Combinatorial Engineering of Yarrowia lipolytica as a Promising Cell Biorefinery Platform for the de novo Production of Multi-Purpose Long Chain Dicarboxylic Acids." *Fermentation* 2017, 3(3), 40, 30 pages.
Beopoulos et al., "Yarrowia lipolytica as a model for bio-oil production." *Progress in Lipid Research* 2009, 48(6), 375-87.
Blanchin-Roland et al., "Two upstream activation sequences control the expression of the XPR2 gene in the yeast Yarrowia lipolytica." *Molecular and Cellular Biology* 1994, 14(1), 327-38.
Blazeck et al., "Generalizing a hybrid synthetic promoter approach in Yarrowia lipolytica." *Applied Microbiology and Biotechnology* 2013, 97(7), 3037-52.
Blazeck et al., "Tuning Gene Expression in Yarrowia lipolytica by a Hybrid Promoter Approach." *Applied and Environmental Microbiology* 2011, 77(22), 7905-14.
Bordes et al., "A new recombinant protein expression system for high-throughput screening in the yeast Yarrowia lipolytica" *J. Microbiological Methods* 2007, 70(3), 493-502.
Chen et al., "One-step transformation of the dimorphic yeast Yarrowia lipolytica" *Applied Microbiology & Biotechnology* 1997, 48, 232-235.
Chen, Liang-Jwu and Emil M. Orozco, "Recognition of prokaryotic transcription terminators by spinach chloroplast RNA polymerase" *Nucleic Acids Research* 1988, 16, 8411-8431.
Dobrzyn, Agnieszka and James M. Ntambi, "The role of stearoyl-CoA desaturase in the control of metabolism." *Prostaglandins Leukot Essent Fatty Acids* 2005, 73(1), 35-41.
Friedlander et al., "Engineering of a high lipid producing Yarrowia lipolytica strain" *Biotechnology for Biofuels* 2016, 9:77, 12 pages.
Hong et al., "Engineering Yarrowia lipolytica to express secretory invertase with strong FBA1IN promoter: Secretory invertase expression with FBA1 In promoter from Y. lipolytica." *Yeast* 2012, 29(2), 59-72.
Jakobiak et al., "The Bacterial Paromomycin Resistance Gene, aphH, as a Dominant Selectable Marker in Volvox carteri" *Protist* 2004, 155, 381-93.
Juretzek et al., "Comparison of Promoters Suitable for Regulated Overexpression of β-Galactosidase in the Alkane-Utilizing Yeast Yarrowia lipolytica." *Biotechnol Bioprocess Eng.* 2000, 5, 320-326.
Larroude et al., "Synthetic biology tools for engineering Yarrowia lipolytica." *Biotechnology Advances* 2018, 36(8):2150-64.
Livak, Kenneth J. and Thomas D. Schmittgen, "Analysis of Relative Gene Expression Data Using RealTime Quantitative PCR and the $2^{-\Delta\Delta c_T}$ Method" *Methods* 2001, 25(4):402-8.
Madzak et al., "Strong Hybrid Promoters and Integrative Expression/Secretion Vectors for Quasi-Constitutive Expression of Heterologous Proteins in the Yeast Yarrowia lipolytica" *J. Mol. Microbiol. Biotechnol.* 2000, 2(2), 207-216.

(Continued)

*Primary Examiner* — Robert B Mondesi
*Assistant Examiner* — Todd M Epstein
(74) *Attorney, Agent, or Firm* — Norton Rose Fulbright US LLP

(57) ABSTRACT

The current methods and compositions provide for nucleotide sequences of promoters from *Yarrowia lipolytica* which may be used to drive gene expression in a cell. In some aspects, the promoters are useful for modulating lipid production in oleaginous organisms such as yeast.

22 Claims, 9 Drawing Sheets
Specification includes a Sequence Listing.

(56) References Cited

OTHER PUBLICATIONS

Madzak, Catherine, "Yarrowia lipolytica: recent achievements in heterologous protein expression and pathway engineering" *Applied Microbiology and Biotechnology* 2015, 99(11), 4559-77.

Mandel, M. and A. Higa, "Calcium-dependent bacteriophage DNA infection" *J. Molecular Biology* 1970, 53, 159-162.

Morrison, D.A., "[21] Transformation and preservation of competent bacterial cells by freezing" *Methods in Enzymology* 1979, 68, 326-331.

Müller et al., "Comparison of Expression Systems in the Yeasts *Saccharomyces cerevisiae*, Hansenula polymorpha, Klyveromyces lactis, Schizosaccharomyces pombe and Yarrowia lipolytica. Cloning of Two Novel Promoters from Yarrowia lipolytica." *Yeast* 1998, 14(14), 1267-83.

Nicaud, Jean-Marc, "Yarrowia lipolytica" *Yeast* 2012, 29, 409-418.

Ogrydziak et al., "Alkaline Extracellular Protease Produced by Saccharomycopsis lipolytica CX161-1B." *J Gen Microbiol* 1982, 128(6), 1225-34.

Sassi et al., "Deciphering how LIP2 and POX2 promoters can optimally regulate recombinant protein production in the yeast Yarrowia lipolytica." *Microbial Cell Factories* 2016, 15:159, 11 pages.

Shabbir Hussain et al., "Engineering Promoter Architecture in Oleaginous Yeast Yarrowia lipolytica." *ACS Synthetic Biology* 2016, 5(3), 213-23.

Stemmer et al., "Single-step assembly of a gene and entire plasmid from large numbers of oligodeoxyribonucleotides" *Gene* 1995, 164, 49-53.

Tai, Mitchell and Gregory Stephanopoulos. "Engineering the push and pull of lipid biosynthesis in oleaginous yeast Yarrowia lipolytica for biofuel production" *Metabolic Engineering* 2013, 15, 1-9.

Thevenieau et al., "Applications of the Non-Conventional Yeast Yarrowia lipolytica." *Yeast Biotechnology: Diversity and Applications,* edited by Tulasi Satyanarayana and Gotthard Kunze. Springer Netherlands, 2009, p. 589-613.

Trassaert et al. "New inducible promoter for gene expression and synthetic biology in Yarrowia lipolytica" *Microb Cell Fact* 2017, 16(1), 141, 17pages.

Tsakraklides et al. "Improved Gene Targeting through Cell Cycle Synchronization" *PLOS ONE* 2015, 10(7):e0133434, 11 pages.

Tsakraklides et al., "High-oleate yeast oil without polyunsaturated fatty acids" Biotechnology for Biofuels 2018, 11:131, 11 pages.

Wartmann et al., "High-level production and secretion of recombinant proteins by the dimorphic yeast Arxula adeninivorans" *FEMS Yeast Research* 2002, 2, 363-369.

Wong et al., "YaliBricks, a versatile genetic toolkit for streamlined and rapid pathway engineering in Yarrowia lipolytica." *Metabolic Engineering Communications* 2017, 5, 68-77.

Xue et al., "Production of omega-3 eicosapentaenoic acid by metabolic engineering of Yarrowia lipolytica." *Nature Biotechnology* 2013, 31(8), 734-40.

* cited by examiner

SEQ ID NO:1  (PR104 YALI0E24189g    -1000 to -1)

ATTGACAGATGAATCCCGGTAAGCCGCCCGGGGATACTACATTTTCGACTTTG
ACAGGTTGCAGCGCGTCCGCCCTACAGTATAGTGGGATATGACAGAGTATCAAATC
AAGCGCGAGGAGGGACAGTTAGGAGTATTACAAGCGGACAAGGCGAGTCAGTTCAT
TTTGTCTGTCTACAAGTCGACATGTTTCAGATTACCAATTTGAAAAAATGGGTTTTG
GAGTGATCTACGAGGCACAGTCTTCAACGAGGCACAGTCTTCTACAAGGCACAGCG
TTCTACGAGTCACAGCTTTCTACACTCTCAACCTCACTGCTACTGTACAAGTACGATA
ATACCCAAAGGTGATCGCCGACTCTGATACTGTACTAATTTATGTACTGTTCTGTAA
AAAATCTCAATGGCAACAGTCGTCTCAAAACCCCTGGCCATTTCAACATCGGCATGA
GCTCACAGTGCTGTCACAGATATACCACATGGTAGAGCTGTAACTTTGTAGAGAATG
TCGATGTGGGAACAAGACATCTCTACCATTAGAGAGATTAATAACACGGGGTCCCA
CTTCTACAATTTGTCTCACTCTTTATACAATCTCAATACGCCCGAACCTATACCGATT
GGATACTGGTAAAGTACATACATTCAATAACTACCGTCATAACACTACTTCAACCAC
CATACAGACTTCTTTGGTTGCCTCGTTTGTAAACATCTTCACCTAAATAGACCACCAG
CACCTCTGCTTGCACTCACCCTAAGCCACTACCCCACACTAACTCTGAACGTGACCG
TCCCCTCAGCTCCGTGGCCATCTAAAGATCCCGCGTTAGCCGTTCCCCAGAGACAAA
ATAAACCTGTTTAACTAACAATACTACAATAGGGGCAAAAAAGGGGCTCGGTATG
CTGGGCATCACGTGATTAGATCAACCCTCCACCCCCGCCAAAAGGTTTGTGCTGCTC
GTGACCATAACCTCATTCGGTTATTTCCACCTTATC

FIG. 1

SEQ ID NO:2 (PR105 YALI0B16522g    -1000 to -1)

TACGTCATTTTCCCTCACAGCGTGCGTCCTATAGGCACATAAACTTGCCCTTC
ATAAATCCCACAGCATACATCAAAAGCCGCTTTATGTGCGCGTAGAAGCCGCCATTT
GTGCGTGCGAGGCGTAGGTAAGAGAACTCGAGCGGTGTCGGAGCTTTATATACCGG
TATCGGTGCCCCTATTAGACTTGCTAGTTTAGCTGGTTTTCTAGATCTACGGTAGCG
CACTTGGGGTCATGGGCATTTTCCACCTAAGCGAGCAATATTTTCAGAGATCAAGGT
CCGTCTAGAACCGTTAGGTGGCATGTTTCTCCTCGAACTCCTTGTCTGCAACGTGTAC
AGCTGGACCCGTTTGGTGGGGTAAAGACAAACGAGGCAGACTCAGCGAGCACAGAA
AAAGGGCAATGGGGAAAAAGCAAAGTCTAAAAAGCTAAAATACGTGGAGCCAT
GGGCAAGCAATAAGGTCTGTGTAAGGCACTTTTCGGCGAGAGAGAAGTGGAACAGT
AGCTCAGAAGAGAATATGCATCTATGCCCTTCTAGGGCTGTATTTCTTTTTCCCAGTT
GATCGGGCTTGGTCACGCTACTTGACCGAATCAGCCATCACTTAGTGTGTGTCTAAT
GCTAGCCAAGAGCTAACGGTCAGAGTTGCATGCATTCGGTGCTGAAGGAATAATCA
GGGAAGTAACCATCTGTATCAAATGCTCTCTCCTTTGACAAATATTGCCGGAAAT
CAGTCCACATGAGTATTGCACCTCCTAAATTTGCCTCTCCTCTTTCCCCACACGGCTA
TCTTGTTTTACCTGCACCAGTAAACACAGTTCACTGCGCTGCACGGCTAACCTAGAG
CATGTTACACCCGGCCACCTTGGCTTATAAACGTTGGTATGGGACGCTAGTGTAGAC
TCTAAAAGTGTTGTTGCAAAGAAATCCATCTCATTTGAACTGAGCGGGTTTTATTG
CACATCTTTACACCTCTCTCTTGCATCTTTTGTGAAC

FIG. 2

SEQ ID NO:3 (PR106 YALI0B21010g    -1000 to -1)

TAGCTTATCCAAGCACATACAGTACTCGCAGCTTCTACTGTAGCTACGTTGTA
GGTATGAAGAGCCAAATGAAAAAACTCTTGCGAAAATTTTCGTCAATAGCCTGTTGT
ATAGCACGAAAAAAGGCACGTGTATCTTCGTTACCTATTCAAGAAGCAATAGGCGG
CACGTAACCGAGTGTGAGCGGGCTGTGTAAGAATATCAGGGAGATAGTCCTGAGGT
GGACTAATGAGTACAGTAGTTGTAGTCATTGGAGCAACAGATAGTATATTACGAAT
ATATACGTGTACAAGTACAAGTACAAGTACAAGTACAGGTGTAGCCTCCCTTCACTA
TACGTAACCCACAGTCAGACATGACTCAATACCGTCAATGCCGGACTTATTTGTACC
CGGAGATGAGGCTGGGAGGGCGCTGCCTGACTCAGACCTCCCTCCACACCGTACA
CAGCCTGGCGTGATTGCCGTGTTTGTGTTACACGATGCCCTCCACAGTTAGTAGTAC
GAGGCGTAAACGCCACATTAACGCACAAGACGTGATACAACGTTGTTTGAGGCCAC
AAAGCTTGTCATGCGCAACACTCCCCATTCCGAAGGTGTATCCGCTCTCGTGCCTGT
TGGTTAAGATTTGGGGGAGTGTTTGACGAGACCTGTTTTCATCCTGAATGATCATCT
ACCAGTATTCTACGAGTGATATCTGCCAAGACTTCGTCTGCAAGTTCTGTCTAACCTC
CTCTTGGCATGCGTCGATAGGAGTATCACCATATGCACGATAGAGACCATGTGGGG
GTGTCCGGGGAATCAAGGTTACCTTACCGAGGACCCCAAGATCCCGAAATTAAAGC
CTATATTTATCGCGTATGTCCGAACCAAAGCCACCTTTCAATACCACCGTCCATACG
GTTGTGCAAGCCACGATGAGTTATATTCGGGCTGGAGAGTGGCTTGACAGACAGTAT
ATAATCTTGGGTGAGGTGTGTGCGACCGGATTATTCTCGCA

FIG. 3

SEQ ID NO:4 (PR107 YALI0C01411g   -1000 to -1)

TCACGAAGATTCGAACGGCGGAATGACTAACAAGCGGCGGAAAAGCTCGAA
CCACAGTCTAGAACATGTGGGGTGACATGCAGATAATACGACGAAGATGATCATGG
GTTCAGGTTTGTTATACGTCATAATACGAGGATTGTATAGGTGTCTTGTGCTCGTACT
ACAAAATATACCGTATCGTACGTTTATAGGGCACTAAGGCGGCGCGAGGCTAGGGT
TTTCAGGGCCATTTTAGCCGACTCCCCCAATTTTGCTGCATCGATGTATCCGTACGAG
TAACCTTAAGTAAAAGTTAAGTAAAATTTGGGGGTATGTTTTTCTAAAGTGTGGAAA
AGCGGCAAATTTCACGGTGCAAGGTGTCTGCTTGAAGATTATATATGTTATGGCTAT
TATTTCGTACATTTTTGTTCATTTTTAGTTTCTGTGGGAGTTCGGGAACCCTGTATTTG
AACCCCCAGCCGACTTTTGTTTCTAACTAAAGGGTAAGTAATTGGGATAATTGATTT
GGGGGTCTGTTCAAACCTCCAGTTTACCACTGCAAGACCTTTTGTCTCTTTTTAGCTT
CTTGATACTTCAATTCATGGGACAATTTTTCCAAGTGAGTTCACTCGGCCGGCCGGT
CTAATTTTATCAATCTCCAATCTCGACATCGCACAGCATCCATTTCTAACCACAGCT
CTAGTTAACTACAGTACAATTATTTCTCTCTTTTCTTCCACTAATTTTTATAAGGTTA
CTGAAGCAACGCGATCAATCACAGTTTGTGTTGTGTTGTGACCACCCTATCATATCTT
CTCCACCTAATCTTCTGCAACTTTTACACACCTTTGCCTCGACACTCGCCACCCTA
GATACCCTCTGAGAGATACTATCGGATATTCCCTGGACTAGAGCTTCTACCAAGAGA
TACCAAGGTATGTGGACCGGCGCCCATGTTGCGATACCACCGCTCTATTCATTGTGA
TACCTCCAGCCATTATCATACTAACACAG

FIG. 4

SEQ ID NO:5 (PR108 YALI0A04631g    -370 to -1)

AAGAGACAGGGTCTACTTCATGGGTCACTCAAACATTGTATATTAGTAATAA
TTGATCTAATCATAGACGAGCTACAAGTACCAGTACTGAAACCCATGCAGATGATTC
CTATTATCTCCAGAGAGAATCTGCTGTCTAATCCATGACTCTTACACACAAATGAAG
AGTCAGATCCAAAGTCAGTATCTATAGTTAGATCCACAAAGTAGTCTTGTGGGTATC
TGGTGGAACCGCGTTATTACACAATATATCAGCAAATGTACATTTTTTTCTCACGTG
ATGACACACTCACATGTGATTTGCACGTGACTACATAAACCTTGCGTGGAAATAACT
GCCGCGATGTGTTTCATGTGTTTCGTTTCCCG

FIG. 5

SEQ ID NO:6 (PR109 YALI0A12815g  -1000 to -1)

GAATTGTCTGGGATATTCAAAGGTGAATAATTGCACTTGAAGTTGCCAAATT
GTGCAAAAAATCAGTGATGCCTGAAGAAAAAAGGTCCCACCGAGATTCGAACTCG
GGACCTTAAGATTTGCAATCTCACGCGCTACCGCTGTGCCATAGGACCGGATTTTGA
GAGGAGCTCGAGGTTTTACTGCGGTATCCGCAAAGCGTCAAAAATCATCATTAGAAT
AAAAAAAATCATTAGAATTAAAAAAAAAAAAAACTCTCAAATTCCGCAATTCCAGA
GGATTTTTGACACATTAAATACAGTCATGGTGATTAAACAGGTTCAAGAAACAGCAT
AGAAAGGCTTTCACTTCAATATCCCCATGTATCATGAGTAGTTGTGTATGGTTAGAA
AATGAAAAGTCCGCAGAATCATTTTCTGTATGGAGACTTCCTAGCGCTTGGGGGAG
AGGGGGAATGACCGACGGGGCTCTGAATAACTGCTATCTAACTTCATACAGAAATA
CAGTCTCTCTTAAAAGTGAAGTATTCATTAATACAGCACGATAATGTCTAATTAGAA
GGAGTATCAAATTGGAAAGAGTATCAAAAACTGCAAGACCTGGAGAGTTGCTTACC
AACAGGATGGAGGAACTACTCATCTTGACATTACAACTGTCGGTCTTTGCCTCATGT
TTCATTATATCCTCAGTCAGTTCATTATATCCTCAGTCAAGTCACCTTAATCCAGGGT
TGTCTTCTTAATCCTGGGTTGTCTAATCCCGAGTTGTCTTCTTATTCATTCTGTCACCA
TCTTAAGCATCTGTGTCACTGTGTCACTATGTTTCCAACACCCGCCGAGAAGATGG
CGGCGTCGCCAGTTTCGAGCTCAATCTACGTTACAACCAGCTTTTGAAACAACGATA
TACACTGAAATGCCAGGTTCAGGGCATCAACGACAGCAACGACGGGCTCTTGCACC
GGCTCAATAAGGCTTGCGATACCAGACTTGCGGCCGAA

FIG. 6

SEQ ID NO:7 (PR110 YALI0B19800g    -1000 to -1)

CCAACTCTCCCAAGCGTCTTTGAATGCACTGAATGTTGGAAAGACGAAATGT
ATCGGTTCTATTCCATCTATTTCAAATCAAGTTCATTTCATTCTCACACCACAAAGTC
GACTTTTCGATTTCTGCAACCGACTTTGGACAGTCGGCAAACTTTATCGTTGTCTCGC
GTGGCAATGTTTTTGCCTTTTTTACAGTCGCTAGACTTTTCTTTTCATTATCATCTTTA
GCAGCAGTATAAGCTCCTGACAGCCAAAAGGAGAAGGACAACAGATAGCGACTTGT
GCTCATCAATAGACAAGGGGAGCTGGCCGAGGTCAACAGGGTTGGCTTTAGTTATA
GTCGGGTATGTCAGGCAACTGAACTGAGACAAGCAATCCCCGTAAATATCATTACCT
ATAGCCACCCGCTGGGGCCTCCCTACAGCCACACAGCGTCACATGGCACAGCCTTAT
CACCCCCCGATATCGCTGCTAACGCTGGATCCATGCTTCTGGAGCGTCAACTTATCT
GGCGCGTAGCCAATCACAGCCCAGCCTCTTTATCAAGGAACCATGCGTCCAACAAG
CGAAGGGTCGGTTGCATGGTCATTTCAACTTTATGCCGAGCCCACCGGGGTCATTTT
ACTTTTGTCATCTTGCGGAATAAAGACGTCATGCACTATGAGGCATATATCGGTTAG
AGGACCAGATACGCGGGCCCAGTAAAAATGTCAGTTTCGCGCCCACAAGGCACGGA
CACAGCGTAATATTAAGCATCCCCTCTTATCTCCAAGCCTTATCTAAATAGCACGGC
TCTGGACTGCCGTCTTTAGAGCTATCTATATTAGCGTTCCAAACACATTAACGTTAG
GAGGTTATTACGGGCTAAGCTTCGCTCTGACGTATGAACCCAATAAACTCACATTTC
TCACACTACTCATACACCTGTTGTGGGGAACTCATCACGTATATATAGAGCCATACA
ATCCTACGTAATGAGACCCATCACTCATCCTGTGCT

FIG. 7

SEQUENCE LISTING

```
<160> NUMBER OF SEQ ID NOS: 7

<210> SEQ ID NO 1
<211> LENGTH: 1000
<212> TYPE: DNA
<213> ORGANISM: Yarrowia lipolytica

<400> SEQUENCE: 1
attgacagat gaatcccggt aagccgcccg gggatactac attttcgact ttgacaggtt      60
gcagcgcgtc cgccctacag tatagtggga tatgacagag tatcaaatca agcgcgagga     120
gggacagtta ggagtattac aagcggacaa ggcgagtcag ttcattttgt ctgtctacaa     180
gtcgacatgt ttcagattac caatttgaaa aaatgggttt ttggagtgat ctacgaggca     240
cagtcttcaa cgaggcacag tcttctacaa ggcacagcgt tctacgagtc acagctttct     300
acactctcaa cctcactgct actgtacaag tacgataata cccaaaggtg atcgccgact     360
ctgatactgt actaatttat gtactgttct gtaaaaaatc tcaatggcaa cagtcgtctc     420 aaaaccctg gccatttcaa catcggcatg agctcacagt gctgtcacag atataccaca      480
tggtagagct gtaactttgt agagaatgtc gatgtgggaa caagacatct ctaccattag     540
agagattaat aacacggggt cccacttcta caatttgtct cactctttat acaatctcaa     600
tacgcccgaa cctataccga ttggatactg gtaaagtaca tacattcaat aactaccgtc     660
```

| | |
|---|---|
| ataacactac ttcaaccacc atacagactt ctttggttgc ctcgtttgta aacatcttca | 720 |
| cctaaataga ccaccagcac ctctgcttgc actcaccctca agccactacc ccacactaac | 780 |
| tctgaacgtg accgtcccct cagctccgtg gccatctaaa gatcccgcgt tagccgttcc | 840 |
| ccagagacaa aataaacctg tttaactaac aatactacaa taggggcaaa aaaagggggct | 900 |
| cggtatgctg ggcatcacgt gattagatca accctccacc cccgccaaaa ggtttgtgct | 960 |
| gctcgtgacc ataacctcat tcggttattt ccaccttatc | 1000 |

<210> SEQ ID NO 2
<211> LENGTH: 1000
<212> TYPE: DNA
<213> ORGANISM: Yarrowia lipolytica

<400> SEQUENCE: 2

| | |
|---|---|
| tacgtcattt tccctcacag cgtgcgtcct ataggcacat aaacttgccc ttcataaatc | 60 |
| ccacagcata catcaaaagc cgctttatgt gcgcgtagaa gccgccattt gtgcgtgcga | 120 |
| ggcgtaggta agagaactcg agcggtgtcg gagctttata taccggtatc ggtgccccct | 180 |
| attagacttg ctagtttagc tggttttcta gatctacggt agcgcacttg gggtcatggg | 240 |
| cattttccac ctaagcgagc aatatttcca gagatcaagg tccgtctaga accgttaggt | 300 |
| ggcatgtttc tcctcgaact ccttgtctgc aacgtgtaca gctggacccg tttggtgggg | 360 |
| taaagacaaa cgaggcagac tcagcgagca cagaaaaaag ggcaatgggg aaaaaagcaa | 420 |
| agtctaaaaa gctaaaatac gtggagccat gggcaagcaa taaggtctgt gtaaggcact | 480 |
| tttcggcgag agagaagtgg aacagtagct cagaagagaa tatgcatcta tgcccttcta | 540 |
| gggctgtatt tcttttttccc agttgatcgg gcttggtcac gctacttgac cgaatcagcc | 600 |
| atcacttagt gtgtgtctaa tgctagccaa gagctaacgg tcagagttgc atgcattcgg | 660 |
| tgctgaagga ataatcaggg aagtaaccat ctgtatcaaa tgctctctct cctttgacaa | 720 |
| atattgccgg aaatcagtcc acatgagtat tgcacctcct aaatttgcct ctcctctttc | 780 |
| cccacacggc tatcttgttt tacctgcacc agtaaacaca gttcactgcg ctgcacggct | 840 |
| aacctagagc atgttacacc cggccaccctt ggcttataaa cgttggtatg ggacgctagt | 900 |
| gtagactcta aaagtgttgt tgcaaagaaa tccatctcat ttgaactgag cgggttttta | 960 |
| ttgcacatct ttacacctct ctcttgcatc ttttgtgaac | 1000 |

<210> SEQ ID NO 3
<211> LENGTH: 1000
<212> TYPE: DNA
<213> ORGANISM: Yarrowia lipolytica

<400> SEQUENCE: 3

| | |
|---|---|
| tagcttatcc aagcacatac agtactcgca gcttctactg tagctacgtt gtaggtatga | 60 |
| agagccaaat gaaaaaactc ttgcgaaaat tttcgtcaat agcctgttgt atagcacgaa | 120 |
| aaaaggcacg tgtatcttcg ttacctattc aagaagcaat aggcggcacg taaccgagtg | 180 |
| tgagcgggct gtgtaagaat atcagggaga tagtcctgag gtggactaat gagtacagta | 240 |
| gttgtagtca ttggagcaac agatagtata ttacgaatat atacgtgtac aagtacaagt | 300 |
| acaagtacaa gtacaggtgt agcctcccctt cactatacgt aacccacagt cagacatgac | 360 |
| tcaataccgt caatgccgga cttatttgta cccggagatg aggctgggag gggcgctgcc | 420 |
| tgactcagac ctccctccac accgtacaca gcctggcgtg attgccgtgt ttgtgttaca | 480 |
| cgatgccctc cacagttagt agtacgaggc gtaaacgcca cattaacgca caagacgtga | 540 |

-continued

```
tacaacgttg tttgaggcca caaagcttgt catgcgcaac actccccatt ccgaaggtgt    600
atccgctctc gtgcctgttg gttaagattt gggggagtgt ttgacgagac ctgttttcat    660
cctgaatgat catctaccag tattctacga gtgatatctg ccaagacttc gtctgcaagt    720
tctgtctaac ctcctcttgg catgcgtcga taggagtatc accatatgca cgatagagac    780
catgtggggg tgtccgggga atcaaggtta ccttaccgag gaccccaaga tcccgaaatt    840
aaagcctata tttatcgcgt atgtccgaac caaagccacc tttcaatacc accgtccata    900
cggttgtgca agccacgatg agttatattc gggctggaga gtggcttgac agacagtata    960
taatcttggg tgaggtgtgt gcgaccggat tattctcgca                         1000
```

<210> SEQ ID NO 4
<211> LENGTH: 1000
<212> TYPE: DNA
<213> ORGANISM: Yarrowia lipolytica

<400> SEQUENCE: 4

```
tcacgaagat tcgaacggcg gaatgactaa caagcggcgg aaaagctcga accacagtct    60
agaacatgtg gggtgacatg cagataatac gacgaagatg atcatgggtt caggtttgtt    120
atacgtcata atacgaggat tgtataggtg tcttgtgctc gtactacaaa atataccgta    180
tcgtacgttt atagggcact aaggcggcgc gaggctaggg ttttcagggc cattttagcc    240
gactccccca attttgctgc atcgatgtat ccgtacgagt aaccttaagt aaaagttaag    300
taaaatttgg gggtatgttt ttctaaagtg tggaaaagcg gcaaatttca cggtgcaagg    360
tgtctgcttg aagattatat atgttatggc tattatttcg tacattttg ttcatttta    420 gtttctgtgg gagttcggga accctgtatt tgaaccccca gccgactttt gtttctaact    480
aaagggtaag taattgggat aattgatttg ggggtctgtt caaacctcca gtttaccact    540
gcaagacctt tgtctctttt ttagcttctt gatacttcaa ttcatgggac aattttccca    600
agtgagttca ctcggccggc cggtctaatt ttatcaatct ccaatctcga catcgcacag    660
catccatttc tcaaccacag ctctagttaa ctacagtaca attattttct ctcttttctt    720
ccactaattt ttataaggtt actgaagcaa cgcgatcaat cacagttttgt gttgtgttgt    780 gaccacccta tcatatcttc tccacctaat cttctgcaac ttttacacac accttttgcct    840 cgacactcgc cacccctagat accctctgag agatactatc ggatatttcc tggactagag    900
cttctaccaa gagataccaa ggtatgtgga ccggcgccca tgttgcgata ccaccgctct    960
attcattgtg atacctccag ccattatcat actaacacag                         1000
```

<210> SEQ ID NO 5
<211> LENGTH: 370
<212> TYPE: DNA
<213> ORGANISM: Yarrowia lipolytica

<400> SEQUENCE: 5

```
aagagacagg gtctacttca tgggtcactc aaacattgta tattagtaat aattgatcta    60
atcatagacg agctacaagt accagtactg aaacccatgc agatgattcc tattatctcc    120
agagagaatc tgctgtctaa tccatgactc ttacacacaa atgaagagtc agatccaaag    180
tcagtatcta tagttagatc cacaaagtag tcttgtgggt atctggtgga accgcgttat    240
tacacaatat atcagcaaat gtacattttt tttctcacgt gatgacacac tcacatgtga    300
tttgcacgtg actacataaa ccttgcgtgg aaataactgc cgcgatgtgt ttcatgtgtt    360
tcgtttcccg                                                          370
```

<210> SEQ ID NO 6
<211> LENGTH: 1000
<212> TYPE: DNA
<213> ORGANISM: Yarrowia lipolytica

<400> SEQUENCE: 6

```
gaattgtctg ggatattcaa aggtgaataa ttgcacttga agttgccaaa ttgtgcaaaa      60
aatcagtgat gcctgaagaa aaaaaggtcc caccgagatt cgaactcggg accttaagat     120
ttgcaatctc acgcgctacc gctgtgccat aggaccggat tttgagagga gctcgaggtt     180
ttactgcggt atccgcaaag cgtcaaaaat catcattaga ataaaaaaaa tcattagaat     240
taaaaaaaaa aaaactctca aaattccgca attccagagg atttttgaca cattaaatac     300
agtcatggtg attaaacagg ttcaagaaac agcatagaaa ggctttcact tcaatatccc     360
catgtatcat gagtagttgt gtatggttag aaaatgaaaa agtccgcaga atcattttct     420
gtatggagac ttcctagcgc ttgggggaga gggggaatga ccgacggggc tctgaataac     480
tgctatctaa cttcatacag aaatacagtc tctcttaaaa gtgaagtatt cattaataca     540
gcacgataat gtctaattag aaggagtatc aaattggaaa gagtatcaaa aactgcaaga     600
cctggagagt tgcttaccaa caggatggag gaactactca tcttgacatt acaactgtcg     660
gtctttgcct catgtttcat tatatcctca gtcagttcat tatatcctca gtcaagtcac     720
cttaatccag ggttgtcttc ttaatcctgg gttgtctaat cccgagttgt cttcttattc     780
attctgtcac catcttaagc atctgtgtca ctgtgtcact atgttttcca cacccgccg     840
agaagatggc ggcgtcgcca gtttcgagct caatctacgt tacaaccagc ttttgaaaca     900
acgatataca ctgaaatgcc aggttcaggg catcaacgac agcaacgacg ggctcttgca     960
ccggctcaat aaggcttgcg ataccagact tgcggccgaa                          1000
```

<210> SEQ ID NO 7
<211> LENGTH: 1000
<212> TYPE: DNA
<213> ORGANISM: Yarrowia lipolytica

<400> SEQUENCE: 7

```
ccaactctcc caagcgtctt tgaatgcact gaatgttgga agacgaaat gtatcggttc      60
tattccatct atttcaaatc aagttcattt cattctcaca ccacaaagtc gacttttcga     120
tttctgcaac cgactttgga cagtcggcaa actttatcgt tgtctcgcgt ggcaatgttt     180
ttgccttttt tacagtcgct agactttct tttcattatc atctttagca gcagtataag     240
ctcctgacag ccaaaaggag aaggacaaca gatagcgact tgtgctcatc aatagacaag     300
gggagctggc cgaggtcaac agggttggct ttagttatag tcgggtatgt caggcaactg     360
aactgagaca agcaatcccc gtaaatatca ttacctatag ccacccgctg gggcctccct     420
acagccacac agcgtcacat ggcacagcct tatcacccc cgatatcgct gctaacgctg     480
gatccatgct tctggagcgt caacttatct ggcgcgtagc caatcacagc ccagcctctt     540
tatcaaggaa ccatgcgtcc aacaagcgaa gggtcggttg catggtcatt caactttat      600
gccgagccca ccggggtcat tttacttttg tcatcttgcg gaataaagac gtcatgcact     660
atgaggcata tatcggttag aggaccagat acgcgggccc agtaaaaatg tcagtttcgc     720
gcccacaagg cacggacaca gcgtaatatt aagcatcccc tcttatctcc aagccttatc     780
taaatagcac ggctctggac tgccgtcttt agagctatct atattagcgt tccaaacaca     840
ttaacgttag gaggttatta cgggctaagc ttcgctctga cgtatgaacc caataaactc     900
```

```
acatttctca cactactcat acacctgttg tggggaactc atcacgtata tatagagcca    960
tacaatccta cgtaatgaga cccatcactc atcctgtgct                        1000
```

METHODS AND COMPOSITIONS INVOLVING PROMOTERS DERIVED FROM YARROWIA LIPOLYTICA

CROSS-REFERENCE TO RELATED APPLICATIONS

This application claims priority to U.S. Provisional Application No. 62/879,989, filed Jul. 29, 2019, incorporated by reference herein in its entirety.

SEQUENCE LISTING

The instant application contains a Sequence Listing which has been submitted in ASCII format and is hereby incorporated by reference in its entirety. Said ASCII copy, created on Jul. 29, 2020, is named NOVG_P0016US_Seq.txt and is 64,078 bytes in size.

BACKGROUND

Field of the Invention

The disclosure is generally directed to biotechnology. Embodiments pertain to promoter regions from *Yarrowia lipolytica* that direct gene expression of other genes and/or in other organisms.

Description of Related Art

Oleaginous yeasts, such as *Yarrowia lipolytica*, may be engineered for the industrial production of lipids, which are indispensable ingredients in the food and cosmetics industries, and important precursors in the biodiesel and biochemical industries. The lipid yield and composition (i.e. the types of fatty acids in the lipids) of an oleaginous organism can be increased by up-regulating or down-regulating the genes that regulate cellular metabolism and lipid pathways.

Some *Y. lipolytica* promoters have been identified and validated (See, e.g., U.S. Pat. Nos. 7,259,255; 7,264,949; U.S. Patent Publication No. 2012/0289600; US Patent Publication No. 2006/0094102; and Wartmann et al., FEMS YEAST RESEARCH 2:363-69 (2002), all of which are herewith incorporated by reference in their entirety). *Yarrowia*, however, contains hundreds of promoters that have yet to be identified, and many of these promoters may be useful for engineering yeast and other organisms. A promoter may vary considerably between different strains of the same species, and the identification and screening of such genetic polymorphisms provides a richer toolbox for genetic engineering.

One approach to up-regulating a gene is to control its expression using a constitutive promoter. For example, the *Y. lipolytica* diacylglycerol acyltransferase DGA1 may be up-regulated using a strong constitutive promoter (See, e.g., Tai & Stephanopoulos, METABOLIC ENGINEERING 15:1-9 (2013)).

Choosing optimal promoters for controlling gene expression is a critical part of genetic engineering, but different promoters may be optimal for different applications. For example, the optimal promoters for an industrial strain of yeast may not be the same as promoters that are optimal in laboratory strains.

There remains a need for efficient yeast systems that control various phenotypes, for example, increase or reduction in lipid production and modification of lipid composition.

SUMMARY OF THE DISCLOSURE

Here, embodiments include, inter alia, promoter sequences comprising SEQ ID NO:1, 2, 5, 6, 7, or subsequences thereof, that are useful for differential expression of genes of a host cell. The promoters may promote decreased expression of a coding sequence during a lipid accumulation phase of *Yarrowia lipolytica* relative to a growth phase. In some embodiments, the use of such promoters is advantageous when there is a need to eliminate or reduce protein accumulation and/or activity during the lipid production phase of an oleaginous host cell, while maintaining some level of gene expression and/or protein activity during the growth of the cell. This differential expression of genes during the growth cycle of an organism can be used, for example, to optimize lipid yield, lipid composition, or the efficiency of the industrial process involving the organism. A gene, or a sequence of interest such as a coding sequence, can be placed under the control of a promoter sequence comprising SEQ ID NO:1, 2, 5, 6, or 7 or a subsequence thereof to allow transcription of the coding sequence and activity of the resultant protein during an active growth phase of a host cell, while reducing transcription of the coding sequence and/or activity of the result protein during a lipid accumulation phase.

Embodiments include compositions comprising one or more nucleic acid molecules. Embodiments include a nucleic acid molecule comprising one or more sequences (e.g., promoter sequences, coding sequences, etc.). Embodiments also include recombinant, transformed or modified cells, vectors, and/or expression cassettes comprising such nucleic acid molecules.

Embodiments also include methods of expressing a sequence of interest (e.g., a coding sequence), methods of transcribing a sequence, method of regulating transcription, methods of regulating expression, methods of modulating lipid production in a host cell, methods of making a nucleic acid comprising a promoter sequence, methods of using a nucleic acid comprising a promoter sequence, methods of linking two sequences (e.g., a promoter sequence and a coding sequence), methods of regulating expression of a sequence, methods of regulating the activity of a sequence, methods of expressing a sequence in a cell, methods of reducing expression of a sequence in a lipid accumulation phase relative to a growth phase, methods of optimizing lipid production, methods of increasing lipid yield, methods of modifying lipid composition of a cell, methods of culturing a host cell, methods of fermentation, methods of producing lipids, methods of differentially expressing a polypeptide, and improvements of known methods for producing lipids. The steps and embodiments discussed in this disclosure are contemplated as part of any of these methods. The methods, steps and embodiments discussed in this disclosure regarding *Yarrowia lipolytica* are also contemplated for other microbial cells, yeast cells, fungal cells and plant cells. In some embodiments, the methods contemplated here can comprise or exclude any of the following steps: providing a nucleic acid, operably linking to a coding sequence a heterologous nucleic acid sequence, introducing a recombinant coding sequence into a host cell, expressing a coding sequence, generating a nucleic acid molecule comprising a sequence comprising a promoter sequence operably linked to a coding sequence, subjecting a cell to conditions sufficient to express a sequence (e.g., a coding sequence), introducing a promoter sequence into a nucleic acid molecule, and/or culturing a host cell.

In some aspects, the disclosure relates to a nucleic acid molecule comprising a first sequence having at least 70% sequence identity to SEQ ID NO:1, 2, 5, 6, or 7. In some embodiments, the first sequence has at least 80% sequence identity to SEQ ID NO:1, 2, 5, 6, or 7. In some embodiments, the first sequence has 70%, 71%, 72%, 73%, 74%, 75%, 76%, 77%, 78%, 79%, 80%, 81%, 82%, 83%, 84%, 85%, 86%, 87%, 88%, 89%, 90%, 92%, 93%, 94%, 95%, 96%, 97%, 98%, 99% or 100% sequence identity, or any range derivable therein, to SEQ ID NO: 1, 2, 5, 6, or 7. In some embodiments, the first sequence is SEQ ID NO:1, 2, 5, 6 or 7. In some embodiments, the first sequence is linked to a second sequence. In some embodiments, the first sequence is operably linked to a second sequence. In some embodiments, the second sequence is heterologous to the first sequence. In some embodiments the second sequence is from *Yarrowia*. In some embodiments, the second sequence is from *Yarrowia lipolytica*. Yet, in some embodiments, the second sequence is not from *Yarrowia*.

In some aspects, the disclosure relates to a nucleic acid molecule comprising a first sequence having at least 70% sequence identity to a subsequence of SEQ ID NO: 1, 2, 5, 6 or 7. In some embodiments, the first sequence has at least 80% sequence identity to a subsequence of SEQ ID NO:1, 2, 5, 6, or 7. In some embodiments, the first sequence has 70%, 71%, 72%, 73%, 74%, 75%, 76%, 77%, 78%, 79%, 80%, 81%, 82%, 83%, 84%, 85%, 86%, 87%, 88%, 89%, 90%, 92%, 93%, 94%, 95%, 96%, 97%, 98%, 99% or 100% sequence identity, or any range derivable therein, to a subsequence of SEQ ID NO: 1, 2, 5, 6, or 7. In some embodiments, the first sequence is operably linked to a second sequence. In some embodiments, the second sequence is heterologous to the first sequence. In some embodiments, the first sequence is capable of conferring expression of the second sequence. In some embodiments, the second sequence is a coding sequence. In some embodiments, the first sequence is constructed from various promoter functional elements derived from any of SEQ ID NO:1, 2, 5, 6 or 7.

In some aspects, the disclosure relates to vectors comprising a nucleotide sequence disclosed herein, for example, a sequence having at least 70% sequence identity to SEQ ID NO:1, 2, 5, 6 or 7 or a subsequence of SEQ ID NO:1, 2, 5, 6 or 7 or a functional variant of SEQ ID NO:1, 2, 5, 6 or 7. In some embodiments, the vector further comprises a coding sequence. In some embodiments the vector is a plasmid. In other embodiments, the vector is a linear DNA molecule.

Further aspects of the disclosure relate to a cell comprising a nucleic acid molecule comprising SEQ ID NO: 1, 2, 3, 4, 5, 6 or 7 or a sequence that is 70%, 71%, 72%, 73%, 74%, 75%, 76%, 77%, 78%, 79%, 80%, 81%, 82%, 83%, 84%, 85%, 86%, 87%, 88%, 89%, 90%, 92%, 93%, 94%, 95%, 96%, 97%, 98%, 99% or 100% (or any range derivable herein) identical to SEQ ID NO:1, 2, 5, 6 or 7 or a subsequence of SEQ ID NO:1, 2, 5, 6 or 7 or a functional variant of SEQ ID NO:1, 2, 5, 6 or 7. In some embodiments, the cell further comprises a coding sequence. In some embodiments, the nucleic acid molecule is a genome of the cell. In some embodiments, the nucleic acid molecule is a vector within the cell. In some embodiments, the cell is a yeast cell. In some embodiments, the yeast cell is an *Arxula, Aspergillus, Aurantiochytrium, Candida, Claviceps, Cryptococcus, Cunninghamella, Geotrichum, Hansenula, Kluyveromyces, Kodamaea, Leucosporidiella, Lipomyces, Mortierella, Ogataea, Pichia, Prototheca, Rhizopus, Rhodosporidium, Rhodotorula, Saccharomyces, Schizosaccharomyces, Tremella, Trichosporon, Wickerhamomyces*, or *Yarrowia* cell. In some embodiments, the cell is an *Aspergillus niger, Aspergillus orzyae, Aspergillus terreus, Aurantiochytrium limacinum, Candida utilis, Claviceps purpurea, Cryptococcus albidus, Cryptococcus curvatus, Cryptococcus ramirezgomezianus, Cryptococcus terreus, Cryptococcus wieringae, Cunninghamella echinulata, Cunninghamella japonica, Geotrichum fermentans, Hansenula polymorpha, Kluyveromyces lactis, Kluyveromyces marxianus, Kodamaea ohmeri, Leucosporidiella creatinivora, Lipomyces lipofer, Lipomyces starkeyi, Lipomyces tetrasporus, Mortierella isabellina, Mortierella alpina, Ogataea polymorpha, Pichia ciferrii, Pichia guilliermondii, Pichia pastoris, Pichia stipites, Prototheca zopfii, Rhizopus arrhizus, Rhodosporidium babjevae, Rhodosporidium toruloides, Rhodosporidium paludigenum, Rhodotorula glutinis, Rhodotorula mucilaginosa, Saccharomyces cerevisiae, Schizosaccharomyces pombe, Tremella enchepala, Trichosporon cutaneum, Trichosporon fermentans, Wickerhamomyces ciferrii*, or a *Yarrowia lipolytica* cell.

Additional aspects of the disclosure relate to a method of expressing a coding sequence in a cell comprising culturing a cell comprising a nucleic acid molecule comprising the coding sequence, wherein the coding sequence is operably linked to a promoter comprising i) at least 80% sequence identity to SEQ ID NO: 1, 2, 5, 6, or 7; ii) a variant of SEQ ID NO: 1, 2, 5, 6, or 7, or iii) a subsequence of SEQ ID NO: 1, 2, 5, 6, or 7. In some embodiments, the method further comprises subjecting the cell to conditions sufficient to express the coding sequence. In some embodiments, conditions sufficient to express the coding sequence include, for example, culturing the cell, providing nutrients to the cell, and providing one or more growth factors to the cell.

Further aspects of the disclosure relate to a method of linking a promoter sequence to a coding sequence comprising (a) providing (I) a first nucleic acid molecule comprising a promoter sequence comprising i) at least 80% sequence identity to SEQ ID NO: 1, 2, 5, 6, or 7; ii) a variant of SEQ ID NO: 1, 2, 5, 6, or 7, or iii) a subsequence of SEQ ID NO: 1, 2, 5, 6, or 7; and (II) a second nucleic acid molecule comprising a coding sequence; and (b) using the first nucleic acid molecule and the second nucleic acid molecule to generate a third nucleic acid molecule comprising the promoter sequence operably linked to the coding sequence. In some embodiments of the method, the promoter is 70%, 71%, 72%, 73%, 74%, 75%, 76%, 77%, 78%, 79%, 80%, 81%, 82%, 83%, 84%, 85%, 86%, 87%, 88%, 89%, 90%, 92%, 93%, 94%, 95%, 96%, 97%, 98%, 99% or 100% (or any range derivable herein) identical to SEQ ID NO:1, 2, 5, 6 or 7, or a subsequence thereof.

Further aspects of the disclosure involve methods of increasing the lipid yield of a recombinant cell during a fermentation process, wherein the fermentation process comprises a growth phase and a lipid accumulation phase. In some embodiments, the method comprises: introducing into a cell a nucleic acid molecule comprising a promoter sequence operably linked to a coding sequence, wherein the promoter sequence comprises i) a nucleotide sequence having at least 80% sequence identity to SEQ ID NO: 1, 2, 5, 6, or 7, ii) a functional variant of SEQ ID NO: 1, 2, 5, 6, or 7, or iii) a subsequence of SEQ ID NO: 1, 2, 5, 6, or 7, thereby obtaining a recombinant cell and culturing the recombinant cell; and culturing the recombinant cell, wherein the lipid yield of the recombinant cell is increased as compared to a non-recombinant cell of the same species. In some embodiments, the method comprises (a) introducing into a cell a first nucleic acid molecule comprising a promoter sequence comprising i) a sequence having at least 80% sequence identity to SEQ ID NO: 1, 2, 5, 6, or 7, ii) a sequence comprising a functional variant of SEQ ID NO: 1, 2, 5, 6, or 7, or iii) a sequence having at least 80% identity to a subsequence of SEQ ID NO: 1, 2, 5, 6, or 7, thereby obtaining a recombinant cell; (b) in the cell, using the first nucleic acid molecule and a second nucleic acid molecule comprising a coding sequence to generate a third nucleic acid molecule comprising the promoter sequence operably linked to the coding sequence; and (c) culturing the recombinant cell, wherein the lipid yield of the recombinant cell is increased as compared to a non-recombinant cell of the same species. In some embodiments, the promoter confers increased expression or activity of the coding sequence during the growth phase as compared to the lipid accumulation phase.

Additional aspects of the disclosure relate to a method of regulating the expression or activity of a coding sequence during a fermentation process wherein the fermentation process comprises a growth phase and a lipid accumulation phase. In some embodiments, the method comprises: (a) introducing a nucleic acid molecule into a cell, wherein the nucleic acid molecule comprises the coding sequence operably linked to a promoter sequence, wherein the promoter sequence comprises i) a sequence having at least 80% sequence identity to SEQ ID NO: 1, 2, 5, 6, or 7, ii) a sequence comprising a functional variant of SEQ ID NO: 1, 2, 5, 6, or 7 or iii) a sequence having at least 80% sequence identity to a subsequence of SEQ ID NO: 1, 2, 5, 6, or 7; and (b) culturing the cell, thereby regulating expression or activity of the coding sequence. In some embodiments, the method comprises (a) providing a first nucleic acid molecule to a cell, wherein the first nucleic acid comprises a promoter sequence comprising i) a sequence having at least 80% sequence identity to SEQ ID NO: 1, 2, 5, 6, or 7, ii) a sequence comprising a functional variant of SEQ ID NO: 1, 2, 5, 6, or 7 or iii) a sequence having at least 80% identity to a subsequence of SEQ ID NO: 1, 2, 5, 6, or 7; (b) in the cell, using the first nucleic acid molecule and a second nucleic acid molecule comprising a coding sequence to generate a third nucleic acid molecule comprising the promoter sequence operably linked to the coding sequence; and (c) culturing the cell, thereby regulating expression or activity of the coding sequence.

In some embodiments the promoter sequence confers decreased expression or activity of the coding sequence during the lipid accumulation phase as compared to the growth accumulation phase. In some embodiments, the expression or activity of the coding sequence is reduced by at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more in the lipid accumulation phase as compared to the growth phase. In some embodiments, the cell is subjected to fermentation conditions, where the expression or activity of the coding sequence is reduced 96 hours after subjecting the cell to the fermentation conditions relative to 16 hours after subjecting the cell to the fermentation conditions. In some embodiments, the fermentation conditions comprise microaerobic conditions. In some embodiments, the expression or activity of the coding sequence is reduced 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, or 96 hours after providing the first nucleic acid molecule to the cell relative to 1, 2, 3, 4, 5, 6, 7, 8, 9, 10, 11, 12, 13, 14, 15, 16, 17, 18, 19, 20, 21, or 22 hours after providing the first nucleic acid molecule to the cell. In some embodiments, the method further comprises operably linking the coding sequence to the promoter sequence.

The term "growth phase" refers to a phase during which cells are dividing and creating catalytic biomass in non-limited nutrient conditions. The term "lipid accumulation phase" refers to a phase during which there is a decrease in growth rate due to nutrient limitation and excess carbon is diverted to lipid production.

Further aspects relate to a method of making a nucleic acid capable of expressing a coding sequence in a cell. In some embodiments, the method comprises: (a) introducing into the cell a nucleic acid molecule comprising a coding sequence, wherein the coding sequence is operably linked to a promoter sequence comprising i) at least 80% sequence identity to SEQ ID NO: 1, 2, 5, 6, or 7; ii) a variant of SEQ ID NO: SEQ ID NO: 1, 2, 5, 6, or 7, or iii) a subsequence of SEQ ID NO: 1, 2, 5, 6, or 7; and (b) subjecting the cell to conditions sufficient to express the coding sequence. In some embodiments, the method comprises (a) introducing into the cell a nucleic acid molecule comprising a promoter sequence comprising i) a sequence having at least 80% sequence identity to SEQ ID NO: 1, 2, 5, 6, or 7; ii) a sequence comprising a functional variant of SEQ ID NO: SEQ ID NO: 1, 2, 5, 6, or 7, or iii) a sequence comprising at least 80% identity to a subsequence of SEQ ID NO: 1, 2, 5, 6, or 7; (b) in the cell, using the first nucleic acid molecule and a second nucleic acid molecule comprising a coding sequence to generate a third nucleic acid molecule comprising the promoter sequence operably linked to the coding sequence; and (c) subjecting the cell to conditions sufficient to express the coding sequence. In some embodiments, the method further comprises operably linking the coding sequence to the heterologous nucleic acid sequence.

In some embodiments of the disclosed methods, using a first nucleic acid molecule and a second nucleic acid molecule to generate a third nucleic acid molecule comprising a promoter sequence operably linked to a coding sequence comprises introducing the promoter sequence into the second nucleic acid molecule. In some embodiments, the promoter sequence is introduced into the second nucleic acid molecule upstream of the coding sequence. In some embodiments, the promoter sequence is introduced into the second nucleic acid molecule by recombination. In some embodiments, the coding sequence is heterologous to the promoter sequence. In some embodiments, the first nucleic acid molecule is a vector. In some embodiments, the second nucleic acid molecule is a vector. In some embodiments, the second nucleic acid molecule is a nucleic acid molecule of a genome of a cell. In some embodiments, the method further comprises introducing the third nucleic acid molecule to a cell. In some embodiments, the method further comprises subjecting the cell to conditions sufficient to express the coding sequence.

It is contemplated that any method or composition described herein can be implemented with respect to any other method or composition described herein and that different embodiments may be combined.

Use of the one or more sequences or compositions may be employed based on any of the methods described herein. Other embodiments are discussed throughout this application. Any embodiment discussed with respect to one aspect of the disclosure applies to other aspects of the disclosure as well and vice versa. For example, any step in a method described herein can apply to any other method. Moreover, any method described herein may have an exclusion of any step or combination of steps. The embodiments in the Example section are understood to be embodiments that are applicable to all aspects of the technology described herein.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1 depicts the DNA sequence of SEQ ID NO:1, also referred to as promoter PR104 (YALI0E24189g, from −1000 to −1).

FIG. 2 depicts the DNA sequence of SEQ ID NO:2, also referred to as promoter PR105 (YALI0B16522g, from −1000 to −1).

FIG. 3 depicts the DNA sequence of SEQ ID NO:3, also referred to as promoter PR106 (YALI0B21010g, from −1000 to −1).

FIG. 4 depicts the DNA sequence of SEQ ID NO:4 also referred to as promoter PR107 (YALI0C01411g, from −1000 to −1).

FIG. 5 depicts the DNA sequence of SEQ ID NO:5 also referred to as promoter PR108 (YALI0A04631g, from −370 to −1).

FIG. 6 depicts the DNA sequence of SEQ ID NO:6 also referred to as promoter PR109 (YALI0A12815g, from −1000 to−1).

FIG. 7 depicts the DNA sequence of SEQ ID NO:7 also referred to as promoter PR110 (YALI0B19800g, from −1000 to−1).

FIG. 8A shows lipid compositions at the indicated time points for *Y. lipolytica* cells expressing FAD2 controlled by one of 7 promoters (PR104-PR107) compared with a wild-type strain (YB-392) and a Δfad2 strain (NS419). FIG. 8B shows linoleate production for the same time points and cells as FIG. 8A. FIG. 8C shows example microscopic observations of each cell type at 96 hours.

FIG. 9A shows lipid compositions at the indicated time points for *Y. lipolytica* cells expressing OLE1 controlled by one of 4 promoters (PR104, PR105, PR109, and PR110) compared with a wild-type strain (YB-392). FIG. 9B shows OLE1 product production for the same time points and cells as FIG. 9A. FIG. 9C shows example microscopic observations of each cell type at 96 hours.

SEQUENCE LISTING

Figure 8A:
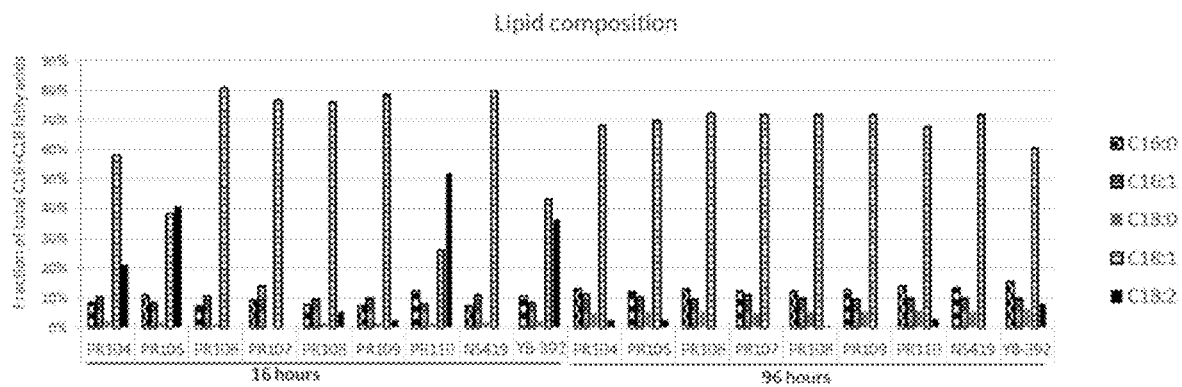
FIGS. 8A-8C show results from experiments described in Example 1.

The instant application contains a Sequence Listing that has been submitted electronically in ASCII format and is hereby incorporated by reference in its entirety. Said ASCII copy, created on Jul. 29, 2020 is named NOVG_P0016US_Seq.txt and is 9,318 bytes in size.

DESCRIPTION OF ILLUSTRATIVE EMBODIMENTS

Increasing efficiency and maximizing lipid metabolism is an important factor in large scale, industrial production of lipids. Researchers have attempted various methods to eliminate or reduce high protein activity during the lipid accumulation phase while maintaining protein activity during growth. One method included gene deletion. Gene deletion, however, has a drawback. It deprives the cell of the corresponding gene/protein activity during the growth phase. Another method is to overexpress a desired activity during lipid accumulation so as to outcompete the unwanted activity. This method is partially effective at best due to the persistence of the undesired protein(s). There exist promoters that can be turned on or off using a culture additive or other external trigger such as galactose induction or erythritol induction (Trassaert et al 2017 New inducible promoter for gene expression and synthetic biology in *Yarrowia lipolytica*. Microb Cell Fact. 16(1):141). However, this latter method requires a process change, often limits the culture media that can be used and adds to the overall cost of the fermentation process.

Accumulation of lipid in *Y. lipolytica* may be triggered by nutrient limitation in the presence of excess carbon. Nitrogen limitation is commonly used for lipid accumulation studies because it is an easily controlled parameter. A *Y. lipolytica* lipid fermentation may comprise two phases: a) growth phase where there is enough nitrogen present for the cells to divide and produce catalytic biomass and, b) lipid production phase where nutrient limitation occurs causing a decrease in growth rate and activation of lipid production. Some pathways (e.g., nucleic acid and protein synthesis) are repressed and others are activated (e.g., fatty acid and triacylglycerol (TAG) synthesis). *Y. lipolytica* cultivations for lipid production may last at least 4 days and involve a high carbon to nitrogen ratio (C/N) such as 50:1 or 75:1.

Through analysis of publicly available transcriptomic data, *Yarrowia lipolytica* transcripts were identified whose abundance dropped at high carbon-to-nitrogen (C:N) ratios. Transcript levels were compared between chemostat growth and D-stat cultivation when C:N ratio reached 25. The promoter regions of these genes were designated as PR104-PR110 (SEQ ID NOs:1-7). The inventors took the 1000 bp (or 370 bp for PR108 (SEQ ID NO:5) where the intergenic region is shorter) upstream of the transcription start site of each of the corresponding genes and used them to drive transcription of genes of interest in order to obtain activity during growth but not during lipid accumulation (a transition involving an increase in the carbon-to-nitrogen ratio). Descriptions of the promoters designated PR104-PR110 are provided in Table 1.

TABLE 1

Description of promoters

| Promoter | Associated gene | Size | Annotation using BLAST/KEGG | Pfam Motif (KEGG) | Ratio (transcript in chemostat/ transcript at high C:N) |
|---|---|---|---|---|---|
| PR104 | YALI0E24189g | −1000 to −1 | hypothetical protein conserved in the *Yarrowia* clade (no hits by homology) | F-box-like; F-box_4; F-box | 100 |
| PR105 | YALI0B16522g | −1000 to −1 | yeast amino acid transporter (similar to uniprot\|P19145 *Saccharomyces cerevisiae* YKR039w GAP1 general amino acid permease) | AA_permease; AA_permease_2 | 51 |
| PR106 | YALI0B21010g | −1000 to −1 | similar to *Candida albicans* putative allantoate permease (by homology) | MFS_1; Herpes_gE; V_ATPase_I; DUF4500 | 40 |
| PR107 | YALI0C01411g | −1000 to −1 | 1,3-beta-glucan synthase [EC:2.4.1.34]; similar to uniprot\|Q6C549 *Yarrowia lipolytica* YALI0E21021g FKS1 component of 1,3-beta-glucan synthase | Glucan_synthase; FKS1_dom1 | 34 |
| PR108 | YALI0A04631g | −370 to −1 | weakly similar to uniprot\|Q6C9E1 *Yarrowia lipolytica* YALI0D11924g, protein with a F-box motif Product: Hypothetical protein of a 30-member gene family, conserved in the *Yarrowia* clade. | F-box-like | 32 |
| PR109 | YALI0A12815g | −1000 to −1 | hypothetical protein conserved in the *Yarrowia* clade | | 28 |
| PR110 | YALI0B19800g | −1000 to −1 | similar to uniprot\|P19145 *Saccharomyces cerevisiae* YKR039W GAP1 General amino acid permease | AA_permease; AA_permease_2 | 20 |

Embodiments herein include placing a sequence or a gene of interest under the control of one of a set of promoters comprising SEQ ID NO:1, 2, 5, 6 or 7 or variants or subsequences thereof that facilitate reduced expression or activity of the sequence or gene of interest during a lipid accumulation phase relative to a growth phase. If the gene represents a native gene, the native locus may be deleted. In some cases, a promoter may be introduced into nucleic acid of a cell, thereby driving expression of a native locus. Differential expression might be used to optimize lipid yield or composition. A key feature of embodiments of the current disclosure is the ability to modulate expression of genes without changing the fermentation process (no additives are required) and that it is tied into the established process of lipid production of *Yarrowia lipolytica*.

The meaning of terms as intended is defined herein below.

I. Definitions

The term "expression" refers to the amount of a nucleic acid or amino acid sequence (e.g., peptide, polypeptide, or protein) in a cell. The increased expression of a gene refers to the increased transcription of that gene. The increased expression of an amino acid sequence, peptide, polypeptide, or protein refers to the increased translation of a nucleic acid encoding the amino sequence, peptide, polypeptide, or protein. Expression may refer to secreted or non-secreted expression products, including polypeptides or metabolites.

The term "expression system" or "expression cassette" refers to nucleic acid molecules containing a desired coding sequence and control sequences in operable linkage, so that hosts transformed or transfected with these sequences are capable of producing the encoded proteins or host cell metabolites. In order to effect transformation, the expression system may be included in a vector; however, the relevant DNA may also be integrated into the host chromosome.

"Expression constructs" or "vectors" or "plasmid" refer to DNA sequences that are required for the transcription of cloned recombinant nucleotide sequences, i.e. of recombinant genes and the translation of their mRNA in a suitable host organism. Expression vectors or plasmids usually comprise an origin for autonomous replication in the host cells, selectable markers (e.g. an amino acid synthesis gene or a gene conferring resistance to antibiotics such as zeocin, kanamycin, G418 or hygromycin), a number of restriction enzyme cleavage sites, a suitable promoter sequence and a transcription terminator, which components are operably linked together. The terms "plasmid" and "vector" as used herein include autonomously replicating nucleotide sequences as well as genome integrating nucleotide sequences. The expression construct of the disclosure specifically comprises a promoter of the disclosure, operably linked to a nucleotide sequence encoding a polypeptide under the transcriptional control of the promoter, which promoter is not natively associated with the coding sequence.

The term "coding sequence" refers to a DNA sequence which codes for a specific amino acid sequence. The terms "coding sequence" and "coding region" are used interchangeably herein. A "coding region of interest" is a coding region which is desired to be expressed.

"Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to: promoters, enhancers, silencers, 5' untranslated leader sequence (e.g., between the transcription start site and translation initiation codon), introns, polyadenylation recognition sequences, RNA processing sites, effector binding sites and stem-loop structures.

The term "heterologous" as used herein with respect to a nucleotide or amino acid sequence refers to a sequence that is not found in a particular context in nature. An example of a heterologous sequence is a nucleotide sequence not natively associated with the promoter according to the disclosure; in some embodiments, a promoter directs or controls the expression of a sequence (i.e., produces an RNA transcript) whose expression is not directed or controlled by that promoter in nature. A polynucleotide comprising a promoter region connected to a heterologous sequence would be considered a hybrid or chimeric polynucleotide. A promoter may be linked to a heterologous sequence from the same organism (e.g., a sequence that is not the same sequence whose expression is controlled by the promoter, such as from a different region of the genome) or a promoter may be linked to a heterologous sequence from a different organism. In some embodiments, the promoter controls or directs the expression of a different gene or coding sequence than it controls or directs in nature.

The term "variant", "functional variant" or "functional promoter variant" as used herein refers to any sequence with a specific sequence identity to a comparable parent sequence. The term can include any sequence derived from SEQ ID NOs:1-7, including sequences that are recombinantly engineered from various promoter elements or promoter regions derived from SEQ ID NOs:1-7 to functionally effect the transcription of an operably linked coding sequence. A variant, functional variant or functional promoter variant may be derived from a parent sequence e.g., by size variation, such as (terminal or non-terminal, such as "interstitional" i.e. with deletions or insertions within the nucleotide sequence) elongation, fragmentation, imitation, hybridization (including combination of sequences). A "functional variant" or a "functional promoter variant" is any variant that retains the ability to drive expression of an operably attached coding sequence.

The term "gene," as used herein, may encompass genomic sequences that contain introns, particularly polynucleotide sequences encoding polypeptide sequences involved in a specific activity. The term further encompasses synthetic nucleic acids that did not derive from genomic sequence. In certain embodiments, the genes lack introns, as they are synthesized based on the known DNA sequence of cDNA and protein sequence or because the gene does not have any introns in nature. In other embodiments, the genes are synthesized, non-native cDNA wherein the codons have been optimized for expression in *Y. lipolytica* based on codon usage. The term can further include nucleic acid molecules comprising upstream, downstream, and/or intron nucleotide sequences, including promoters.

The term "genetic modification" refers to the result of a transformation. Every transformation causes a genetic modification by definition.

The term "homolog," as used herein, refers to (a) nucleic acids having nucleotide substitutions, deletions and/or insertions relative to the unmodified nucleic acid in question and having similar biological and functional activity as the unmodified nucleic acid from which they are derived, and (b) peptides, oligopeptides, polypeptides, proteins, and enzymes having amino acid substitutions, deletions and/or insertions relative to the unmodified protein in question and having similar biological and functional activity as the unmodified protein from which they are derived.

The term "integrated" refers to a nucleic acid that is maintained in a cell as an insertion into the genome of the cell, such as insertion into a chromosome, including insertions into a plastid genome.

The term "introducing" such as in "introducing a coding sequence into a cell" refers to any means by which a heterologous or native nucleic acid is brought into a cell so as to genetically modify or engineer the cell.

The term "vector" refers to the means by which a nucleic acid can be propagated and/or transferred between organisms, cells, or cellular components. Vectors include plasmids, linear DNA fragments, viruses, bacteriophage, proviruses, phagemids, transposons, and artificial chromosomes, and the like, that may or may not be able to replicate autonomously or integrate into a chromosome of a host cell.

"In operable linkage" "operably linked" is a functional linkage between two nucleic acid sequences, such a control sequence (typically a promoter) and the linked sequence (typically, a sequence that encodes a protein, also called a coding sequence). A promoter is in operable linkage (or "operably linked") with a gene if it can mediate transcription of the gene.

The term "native" refers to the composition of a cell or parent cell prior to a transformation event.

The terms "nucleic acid" refers to a polymeric form of nucleotides of any length, either deoxyribonucleotides or ribonucleotides, or analogs thereof. Polynucleotides may have any three-dimensional structure, and may perform any function. The following are non-limiting examples of polynucleotides: coding or non-coding regions of a gene or gene fragment, loci (locus) defined from linkage analysis, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. A polynucleotide may be further modified, such as by conjugation with a labeling component. In all nucleic acid sequences provided herein, U nucleotides are interchangeable with T nucleotides.

The term "parent cell" refers to every cell from which a cell descended. The genome of a cell is comprised of the parent cell's genome and any subsequent genetic modifications to its genome.

As used herein, the term "plasmid" refers to a circular DNA molecule that is physically separate from an organism's genomic DNA. Plasmids may be linearized before being introduced into a host cell (referred to herein as a linearized plasmid). Linearized plasmids may not be self-replicating, but may integrate into and be replicated with the genomic DNA of an organism.

A "promoter" is a nucleic acid region that directs or controls transcription of a nucleic acid sequence on the same polynucleotide. In some embodiments, a promoter directs transcription of an adjacent nucleic acid sequence. As used herein, a promoter may include necessary nucleic acid sequences near the start site of transcription. A promoter also optionally includes distal enhancer or repressor elements, which can be located as much as several thousand base pairs from the start site of transcription. A promoter also optionally includes one or more copies of an upstream activation sequence (UAS).

"Recombinant" refers to a cell, nucleic acid, protein, or vector, which has been modified due to introduction of an exogenous nucleic acid or alteration of a native nucleic acid. Resulting cells, nucleic acids, proteins or vectors are considered recombinant, as are progeny, offspring, duplications or replications of these are also considered recombinant. Thus, e.g., recombinant cells can express genes that are not found within the native (non-recombinant) form of the cell or express native genes differently than those genes are expressed by a non-recombinant cell. Recombinant cells can, without limitation, include recombinant nucleic acids that encode for a gene product or for suppression elements such as mutations, knockouts, antisense, interfering RNA (RNAi), or dsRNA that reduce the levels of active gene product in a cell. A "recombinant nucleic acid" is derived from nucleic acid originally formed in vitro, in general, by the manipulation of nucleic acid, e.g., using polymerases, ligases, exonucleases, and endonucleases, or otherwise is in a form not normally found in nature. Recombinant nucleic acids may be produced, for example, to place two or more nucleic acids in operable linkage Thus, an isolated nucleic acid or an expression vector formed in vitro by ligating DNA molecules that are not normally joined in nature, are both considered recombinant for the purposes of this disclosure. Once a recombinant nucleic acid is made and introduced into a host cell or organism, it may replicate using the in vivo cellular machinery of the host cell; however, such nucleic acids, once produced recombinantly, although subsequently replicated intracellularly, are still considered recombinant for purposes of this disclosure. Additionally, a recombinant nucleic acid refers to nucleotide sequences that comprise an endogenous nucleotide sequence and an exogenous nucleotide sequence; thus, an endogenous gene that has undergone recombination with an exogenous promoter is a recombinant nucleic acid. A "recombinant protein" is a protein made using recombinant techniques, i.e., through the expression of a recombinant nucleic acid.

The term "regulatory region" refers to nucleotide sequences that affect the transcription or translation of a gene but do not encode an amino acid sequence. Regulatory regions include promoters, operators, enhancers, and silencers.

The term "subsequence" refers to a consecutive nucleotide sequence found within a nucleotide sequence that is less than the full-length nucleotide sequence. For example, a subsequence may consist of 100 consecutive nucleotides selected from the nucleotide sequence set forth in SEQ ID NO: 1-7. As used herein, a subsequence consists of at least fifty nucleotides.

"Transformation" refers to the transfer of a nucleic acid into a host organism or the genome of a host organism. Host organisms (and their progeny) containing the transformed nucleic acid fragments are referred to as "recombinant", "transgenic" or "transformed" organisms. Thus, isolated polynucleotides of the present disclosure can be incorporated into recombinant constructs, typically DNA constructs, capable of introduction into and replication in a host cell. Such a construct can be a vector that includes a replication system and sequences that are capable of transcription and translation of a polypeptide-encoding sequence in a given host cell. Typically, expression vectors include, for example, one or more cloned genes under the transcriptional control of 5' and 3' regulatory sequences and a selectable marker. Such vectors also can contain a promoter regulatory region (e.g., a regulatory region controlling inducible or constitutive, environmentally- or developmentally-regulated, or location-specific expression), a transcription initiation start site, a ribosome binding site, a transcription termination site, and/or a polyadenylation signal. Alternatively, a cell may be transformed with a single genetic element, such as a promoter, which may result in genetically stable inheritance upon integrating into the host organism's genome, such as by homologous recombination.

The term "transformed cell" refers to a cell that has undergone a transformation. Thus, a transformed cell comprises the parent's genome and an inheritable genetic modification. Embodiments include progeny and offspring of such transformed cells.

The term "substantially the same" or "not significantly different" refers to a level of expression that is not significantly different than what it is compared to. Alternatively, or in conjunction, the term substantially the same refers to a level of expression that is less than 2, 1.5, or 1.25 fold different than the expression or activity level it is compared to.

The term "promoter region of a *Yarrowia* gene" or "*Yarrowia* promoter region" refers to the 5' upstream untranslated region in front of the 'ATG' translation initiation codon of a *Yarrowia* gene, or sequences derived therefrom, and that is necessary for expression of connected sequence. Thus, it is believed that promoter regions of a *Yarrowia* gene will comprise a portion of the −1000 bp 5' upstream of a *Yarrowia* gene. The sequence of the *Yarrowia* promoter region may correspond exactly to native sequence upstream of the *Yarrowia* gene (i.e., a "wildtype" or "native" *Yarrowia* promoter); alternately, the sequence of the *Yarrowia* promoter region may be "modified" or "mutated", thereby comprising various substitutions, deletions, and/or insertions of one or more nucleotides relative to a wildtype or native *Yarrowia* promoter. These modifications can result in a modified *Yarrowia* promoter having increased, decreased or equivalent promoter activity, when compared to the promoter activity of the corresponding wildtype or native *Yarrowia* promoter. The term "mutant promoter" or "modified promoter" will encompass natural variants and in vitro generated variants obtained using methods well known in the art (e.g., classical mutagenesis, site-directed mutagenesis and "DNA shuffling").

As used herein, the term "complementary" and derivatives thereof are used in reference to pairing of nucleic acids by the well-known rules that A pairs with T or U and C pairs with G. Complement can be "partial" or "complete". In partial complement, only some of the nucleotides are matched according to the base pairing rules; while in complete or total complement, all the bases are matched according to the pairing rule. The degree of complementarity between the nucleic acid strands may have significant an effect on the efficiency and strength of hybridization between two nucleic acid strands as is well known in the art. The efficiency and strength of hybridization depends upon the detection method.

As used herein, the terms "or" and "and/or" are utilized to describe multiple components in combination or exclusive of one another. For example, "x, y, and/or z" can refer to "x" alone, "y" alone, "z" alone, "x, y, and z," "(x and y) or z," "x or (y and z)," or "x or y or z." It is specifically contemplated that x, y, or z may be specifically excluded from an embodiment.

Throughout this application, the term "about" is used according to its plain and ordinary meaning in the area of cell biology to indicate that a value includes the standard deviation of error for the device or method being employed to determine the value.

The term "comprising," which is synonymous with "including," "containing," or "characterized by," is inclusive or open-ended and does not exclude additional, unrecited elements or method steps. The phrase "consisting of" excludes any element, step, or ingredient not specified. The phrase "consisting essentially of" limits the scope of described subject matter to the specified materials or steps and those that do not materially affect its basic and novel characteristics. It is contemplated that embodiments described in the context of the term "comprising" may also be implemented in the context of the term "consisting of" or "consisting essentially of."

It is specifically contemplated that any limitation discussed with respect to one embodiment of the invention may apply to any other embodiment of the invention. Furthermore, any composition of the invention may be used in any method of the invention, and any method of the invention may be used to produce or to utilize any composition of the invention. Aspects of an embodiment set forth in the Examples are also embodiments that may be implemented in the context of embodiments discussed elsewhere in a different Example or elsewhere in the application, such as in the Summary of Invention, Detailed Description of the Embodiments, Claims, and description of Figure Legends.

The use of the word "a" or "an" when used in conjunction with the term "comprising" in the claims and/or the specification may mean "one," but it is also consistent with the meaning of "one or more," "at least one," and "one or more than one."

II. Microbe Engineering

A. Overview

Exogenous promoters and promoter regions such as any derived from SEQ ID NO:1-7 (e.g., sequences comprising or derived from SEQ ID NO: 1, 2, 5, 6, or 7) may be introduced into many different host cells. Suitable host cells are microbial hosts that can be found broadly within the fungal families. Examples of suitable host strains include but are not limited to fungal or yeast species, such as *Arxula, Aspergillus, Aurantiochytrium, Candida, Claviceps, Cryptococcus, Cunninghamella, Hansenula, Kluyveromyces, Leucosporidiella, Lipomyces, Mortierella, Ogataea, Pichia, Prototheca, Rhizopus, Rhodosporidium, Rhodotorula, Saccharomyces, Schizosaccharomyces, Tremella, Trichosporon,* and *Yarrowia. Yarrowia lipolytica* is well-suited for use as the host microorganism because they can accumulate a large percentage of their weight as triacylglycerols.

Microbial expression systems and expression vectors are well known to those skilled in the art. Any such expression vector could be used to introduce the instant promoters into an organism. The promoters may be introduced into appropriate microorganisms via transformation techniques to direct the expression of an operably-linked gene. For example, a promoter can be cloned in a suitable plasmid, and a parent cell can be transformed with the resulting plasmid. This approach can be used to drive the expression of a gene that is either operably linked to the promoter or that becomes operably linked to the promoter following the transformation event. The plasmid is not particularly limited so long as it renders a desired promoter inheritable to the microorganism's progeny.

Vectors or cassettes useful for the transformation of suitable host cells are well known in the art. Typically the vector or cassette contains a gene, sequences directing transcription and translation of a relevant gene including the promoter, a selectable marker, and sequences allowing autonomous replication or chromosomal integration. Suitable vectors comprise a region 5' of the gene harboring the promoter and other transcriptional initiation controls and a region 3' of the DNA fragment which controls transcriptional termination. It is preferred when both control regions are derived from genes homologous to the transformed host cell or from closely related species, although it is to be understood that such control regions need not be derived from the genes native to the specific species chosen as a production host. For example, a *Yarrowia lipolytica* promoter may be used to drive expression in other species of yeast including other oleaginous yeasts.

Promoters, cDNAs, and 3'UTRs, as well as other elements of the vectors, can be generated through cloning techniques using fragments isolated from native sources (Green & Sambrook, Molecular Cloning: A Laboratory Manual, (4th ed., 2012); U.S. Pat. No. 4,683,202; incorporated by reference). Alternatively, elements can be generated synthetically using known methods (Gene 164:49-53 (1995)).

B. Promoter Sequences

Described herein, in some embodiments, are promoter sequences comprising SEQ ID NO:1-7, or subsequences or variants thereof, from *Yarrowia lipolytica* that are useful for modulating lipid production. In some embodiments, described herein are promoter sequences comprising SEQ ID NO: 1, 2, 5, 6, or 7, or subsequences or variants thereof. In some embodiments, promoters described herein facilitate reduced expression or activity of a sequence or gene of interest during a lipid accumulation phase of *Yarrowia lipolytica* relative to a growth phase. The use of such promoters is advantageous when there is a need to eliminate or reduce protein accumulation during the lipid production phase of an oleaginous host cell, while maintaining some level of protein activity during the growth of the cell. This differential expression of genes during the growth cycle can be used to optimize lipid yield or lipid composition. A gene, or a sequence of interest such as a coding sequence is placed under the control of a promoter to allow a given level of transcription and/or activity of the coding sequence during the active growth phase of a host cell and reduced transcription and/or activity of the coding sequence during a lipid accumulation phase (e.g., a phase comprising little to no nitrogen in a culture). Promoters may include the entire length of any of SEQ ID NOS:1-7 or sequences having percent identity to any of SEQ ID NOS:1-7 or may be recombinantly engineered to include transcriptional regulatory regions and/or promoter elements from SEQ ID NOS: 1-7 thereby constituting functional variants of SEQ ID NOS:1-7.

Some embodiments relate to nucleic acid sequences comprising SEQ ID NO: 1-7. Some embodiments also relate to nucleic subsequences derived from SEQ ID NOS:1-7. The nucleic acid sequences or promoters disclosed herein may comprise conservative substitutions, deletions, and/or insertions while still functioning to drive transcription. Thus, a promoter sequence may comprise a nucleotide sequence that is at least or at most 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% (or any derivable range within) identical to any of SEQ ID NO: 1-7, wherein the sequence retains the promoter function and is capable of driving the expression of a coding sequence. A promoter sequence may comprise a nucleotide sequence that is 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% (or any derivable range within) identical to any of SEQ ID NO: 1-7, wherein the sequence retains the promoter function and is capable of driving the expression of a coding sequence To determine the percent identity of two nucleotide sequences, the sequences can be aligned for optimal comparison purposes (e.g., gaps can be introduced in one or both of a first and a second nucleotide sequence for optimal alignment and non-identical sequences can be disregarded for comparison purposes). The nucleotides at corresponding nucleotide positions can then be compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which need to be introduced for the optimal alignment of the two sequences.

The comparison of sequences and determination of percent identity between two sequences can be accomplished using a mathematical algorithm. Exemplary computer programs which can be used to determine identity between two nucleotide sequences include, but are not limited to, the suite of BLAST programs, e.g., BLASTN, MEGABLAST, and Clustal programs, e.g., ClustalW, ClustalX, and Clustal Omega.

Sequence searches are typically carried out using the BLASTN program, when evaluating a given nucleotide sequence relative to nucleotide sequences in the GenBank DNA Sequences and other public databases. An alignment of selected sequences in order to determine "% identity" between two or more sequences is performed using for example, the CLUSTAL-W program.

The abbreviation used throughout the specification to refer to nucleic acids comprising and/or consisting of nucleotide sequences are the conventional one-letter abbreviations. Thus when included in a nucleic acid, the naturally occurring encoding nucleotides are abbreviated as follows: adenine (A), guanine (G), cytosine (C), thymine (T) and uracil (U). Also, the nucleotide sequences presented herein is the 5'→3' direction.

In some cases, the full nucleotide sequence of a promoter is not necessary to drive transcription, and sequences shorter than the promoter's full nucleotide sequence can drive transcription of an operably-linked gene. The minimal portion of a promoter, termed the core promoter, includes a transcription start site, a binding site for a RNA polymerase, and a binding site for a transcription factor. A promoter may comprise a subsequence of any of SEQ ID NOs: 1-7.

A promoter may comprise a subsequence of SEQ ID NO: 5. A promoter may comprise a nucleotide sequence that is at least, is, or is at most 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more identical to 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, or 330 consecutive nucleotides (or any range derivable therein) of SEQ ID NO: 5. Such a subsequence may start at position 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, or 320 of SEQ ID NO:5. Such a subsequence may be 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, or 320 nucleotides in length.

A promoter may comprise a nucleotide sequence that is a subsequence of any of SEQ ID NO: 1, 2, 3, 4, 6, or 7. A promoter may comprise a nucleotide sequence that is at least, is, or is at most 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more identical to 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 600, 700, 800, or 900 consecutive nucleotides (or any range derivable therein) of SEQ ID NO: 1, 2, 3, 4, 6, or 7. Such a subsequence may start at position 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 600, 700, 800, or 900 of any of SEQ ID NOs:1, 2, 3, 4, 6, or 7. Such a subsequence may be 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 600, 700, 800, or 900 nucleotides in length.

The term "subsequence" refers to a consecutive nucleotide sequence found within a nucleotide sequence that is less than the full-length nucleotide sequence. For example, a subsequence may consist of 100 consecutive nucleotides selected from the nucleotide sequence set forth in SEQ II) NO: 1-7.

Additionally, two promoters may be combined. For example, the region of a first promoter that binds an RNA polymerase may be combined with a region of a second promoter that binds one or more transcription factors to create a hybrid promoter. Thus, a subsequence of a promoter may be combined with another promoter to change the transcription factors that regulate the transcription of an operably-linked gene. Thus, a promoter may comprise a nucleotide sequence that is at least or is 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more identical to 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, or 300 consecutive nucleotides found anywhere in SEQ ID NO: 1-7.

Additionally, provided herein is an isolated nucleic acid molecule comprising a promoter region of *Yarrowia* from any of: (a) SEQ ID NO:1; (b) SEQ ID NO:2; (c) SEQ ID NO:3; (d) SEQ ID NO:4; (e) SEQ ID NO:5; (f) SEQ ID NO:6, (g) SEQ ID NO:7 wherein the promoter optionally comprises at least or at most one modification selected from the group consisting of: (i) a deletion at the 3'-terminus and/or the 5'-terminus of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709 or 710 consecutive nucleotides.

A promoter may further comprise and/or be linked to an upstream activation sequence (UAS). A UAS may be capable of strengthening the ability of a promoter sequence to regulate gene expression. A UAS may be configured to increase the expression of a coding sequence operably linked to a promoter sequence (e.g., a sequence comprising any of SEQ ID NOs: 1-7). A promoter may comprise or be linked to 1, 2, 3, 4, 5, 6, 7, 8, 9, or 10 copies of a UAS, or more.

C. Vectors and Vector Components

Vectors for the transformation of microorganisms in accordance with the present disclosure can be prepared by known techniques familiar to those skilled in the art in view of the disclosure herein. A vector typically contains one or more genes, in which each gene codes for the expression of a desired product (the gene product) and is operably linked to one or more control sequences that regulate gene expression (i.e., a promoter), or the vector targets a gene, control sequence, or other nucleotide sequence to a particular location in the recombinant cell.

In general, microbial expression systems and expression vectors containing regulatory sequences that direct high level expression of foreign proteins are well known to those skilled in the art. Any of these could be used to construct chimeric genes, which could then be introduced into appropriate microorganisms via transformation to provide high-level expression of the encoded enzymes.

Any nucleic acid vector may encode a promoter. A plasmid may be a convenient vector because plasmids may be manipulated and replicated in bacterial hosts. In some embodiments, a linear DNA molecule may be a preferable vector, for example, to eliminate plasmid nucleotide sequences prior to transformation. Linear DNA may be obtained from the restriction digest of a plasmid or by PCR amplification. PCR may be used to generate a linear DNA vector by amplifying plasmid DNA, genomic DNA, synthetic DNA, or any other template. For example, PCR may be used to generate a linear DNA vector from overlapping oligonucleotide fragments. Suitable vectors are not limited to DNA; for example, the RNA of a retroviral vector may be utilized to transform a cell with a desired promoter.

The vector may comprise both the promoter and a gene such that the promoter and gene are operably linked. Alternatively, the vector may be designed so that the promoter becomes operably linked to a gene after transformation of the parent cell. For example, a first vector containing the promoter may be designed to recombine with a second vector containing a gene such that successful transformation and recombination events cause the promoter and gene to become operably linked in a host cell. Alternatively, a vector containing the promoter may be designed to recombine with a gene in the genome of the host cell or otherwise integrate into the genome of the host cell. In this embodiment, the exogenous promoter may replace an endogenous promoter.

A vector may comprise one or more additional promoters, genes, and/or other sequences. For example, a vector may comprise a first promoter comprising SEQ ID NO: 1, 2, 5, 6, or 7, or a subsequence or functional variant thereof, operably linked to a first gene, and a second promoter (e.g., a constitutive promoter) operably linked to a second gene. A vector may comprise at least 1, 2, 3, 4, 5, 6, 7, 8, 9, or 10 promoters, or more. A vector may comprise at least 1, 2, 3, 4, 5, 6, 7, 8, 9, or 10 genes, or more. A vector comprising multiple promoters linked to multiple genes may be useful in, for example, reducing the expression of a first gene while simultaneously increasing the expression of a second gene.

1. Control Sequences

Control sequences are nucleic acids that regulate the expression of a coding sequence or direct a gene product to a particular location in or outside a cell. Control sequences that regulate expression include, for example, promoters that regulate the transcription of a coding sequence and terminators that terminate the transcription of a coding sequence. Another control sequence is a 3' untranslated sequence located at the end of a coding sequence that encodes a polyadenylation signal. Control sequences that direct gene products to particular locations include those that encode signal peptides, which direct the protein to which they are attached to a particular location in or outside the cell.

Thus, an exemplary vector design for the expression of a promoter in a microbe contains a coding sequence for a desired gene product (for example, a selectable marker, or an enzyme) in operable linkage with a promoter active in yeast. Alternatively, if the vector does not contain a gene in operable linkage with a promoter, the promoter can be transformed into the cells such that it becomes operably linked to an endogenous gene at the point of vector integration.

The promoter used to express a gene can be the promoter naturally linked to that gene or a different promoter.

The inclusion of a termination region control sequence is optional, and if employed, the choice is primarily one of convenience, as termination regions are relatively interchangeable. The termination region may be native to the transcriptional initiation region (the promoter), may be native to the DNA sequence of interest, or may be obtainable from another source (See, e.g., Chen & Orozco, Nucleic Acids Research 16:8411 (1988)).

2. Genes

Typically, a gene includes a promoter, coding sequence, and termination control sequences. When assembled by recombinant DNA technology, a gene may be termed an expression cassette and may be flanked by restriction sites for convenient insertion into a vector that is used to introduce the recombinant gene into a host cell. The expression cassette can be flanked by DNA sequences from the genome or other nucleic acid target to facilitate stable integration of the expression cassette into the genome by homologous recombination. Alternatively, the vector and its expression cassette may remain unintegrated (e.g., an episome), in which case, the vector typically includes an origin of replication, which is capable of providing for replication of the vector DNA.

A common gene present on a vector is a gene that codes for a protein, the expression of which allows the recombinant cell containing the protein to be differentiated from cells that do not express the protein. Such a gene, and its corresponding gene product, is called a selectable marker or selection marker. Any of a wide variety of selectable markers can be employed in a transgene construct useful for transforming the organisms of the disclosure.

For optimal expression of a recombinant protein, it is beneficial to employ coding sequences that produce mRNA with codons optimally used by the host cell to be transformed. Thus, proper expression of transgenes can require that the codon usage of the transgene matches the specific codon bias of the organism in which the transgene is being expressed. The precise mechanisms underlying this effect are many, but include the proper balancing of available aminoacylated tRNA pools with proteins being synthesized in the cell, coupled with more efficient translation of the transgenic messenger RNA (mRNA) when this need is met. When codon usage in the transgene is not optimized, available tRNA pools are not sufficient to allow for efficient translation of the transgenic mRNA resulting in ribosomal stalling and termination and possible instability of the transgenic mRNA.

D. Homologous Recombination

Homologous recombination may be used to substitute one nucleotide sequence with a different nucleotide sequence. Thus, homologous recombination may be used to substitute all or part of an endogenous promoter that drives the expression of a gene in an organism with all or part of an exogenous promoter. Additionally, homologous recombination may be used to combine two nucleic acids that contain a homologous nucleotide sequence.

Homologous recombination is the ability of complementary DNA sequences to align and exchange regions of homology. For example, transgenic DNA ("donor") containing sequences homologous to the genomic sequences being targeted ("template") may be generated and introduced into an organism to undergo recombination with the organism's genomic sequences.

The ability to carry out homologous recombination in a host organism has many practical implications for what can be carried out at the molecular genetic level and is useful in the generation of microbes that produce a desired product. By its very nature, homologous recombination is a precise gene targeting event; hence, most transgenic lines generated with the same targeting sequence will be essentially identical in terms of phenotype, necessitating the screening of far fewer transformation events. Homologous recombination also targets gene insertion events into the host chromosome, potentially resulting in excellent genetic stability, even in the absence of genetic selection.

Because homologous recombination is a precise gene targeting event, it can be used to precisely modify any nucleotide(s) within a gene or region of interest, so long as sufficient flanking regions have been identified. Therefore, homologous recombination can be used to modify the regulatory sequences impacting the expression of RNA and/or proteins. It can also modify protein coding regions, for example, by modifying enzyme activities such as substrate specificity, binding affinities and Km, and thus, it may affect a desired change in the metabolism of a host cell. Homologous recombination provides a powerful means to manipulate the host genome resulting in gene targeting, gene conversion, gene deletion, gene duplication, gene inversion and exchanging gene expression regulatory elements such as promoters, enhancers and 3'UTRs. Thus, homologous recombination allows for the substitution of an endogenous promoter in an organism with a different promoter. An exogenous promoter may provide advantages over the endogenous promoter; for example, the exogenous promoter may increase or decrease the transcription of an operably-linked gene, or the exogenous promoter may allow for the regulation of transcription by different cellular processes relative to the endogenous promoter.

Homologous recombination can be achieved by using targeting constructs containing pieces of endogenous sequences to "target" the gene or region of interest within the endogenous host cell genome. Such targeting sequences can be located upstream or downstream of the gene or region of interest, or flank the gene/region of interest. Such targeting constructs can be transformed into the host cell as circular plasmid DNA, optionally including nucleotide sequences from the plasmid; linearized DNA, such as a plasmid restriction digest; PCR product, such as the amplification of overlapping oligonucleotides; or any other means of introducing DNA into a cell. In some cases, it may be advantageous to first expose the homologous sequences within the transgenic DNA (donor DNA) by cutting the transgenic DNA with a restriction enzyme, which can increase recombination efficiency and decrease the occurrence of non-specific recombination events. Other methods of increasing recombination efficiency include using PCR to generate transforming transgenic DNA containing linear ends homologous to the genomic sequences being targeted.

E. Transformation

Cells can be transformed by any suitable technique including, e.g., biolistics, electroporation, glass bead transformation, and silicon carbide whisker transformation. Any convenient technique for introducing a transgene into a microorganism can be employed in the present disclosure. Transformation can be achieved by, for example, the method of D. M. Morrison (Methods in Enzymology 68:326 (1979)), the method by increasing permeability of recipient cells for DNA with calcium chloride (Mandel & Higa, J. Molecular Biology, 53:159 (1970)), or the like.

Examples of the expression of transgenes in oleaginous yeast (e.g., *Yarrowia lipolytica*) can be found in the literature (Bordes et al., J. Microbiological Methods, 70:493 (2007); Chen et al., Applied Microbiology & Biotechnology 48:232 (1997)).

Vectors for the transformation of microorganisms can be prepared by known techniques. In one embodiment, an exemplary vector for the expression of a gene in a microorganism comprises a gene encoding a protein in operable linkage with a promoter. Alternatively, if the promoter is not operably linked with the gene of interest, the promoter may be transformed into a cell such that it becomes operably linked to a native gene at the point of vector integration. Additionally, microbes may be transformed with two vectors simultaneously (See, e.g., Protist 155:381-93 (2004)). The transformed cells can be optionally selected based upon their ability to grow in the presence of an antibiotic or other selectable marker under conditions in which untransformed cells would not grow.

F. Promoter Targets

One or more promoters of the present disclosure (e.g., a sequence comprising SEQ ID NO: 1, 2, 5, 6, or 7, or a subsequence or functional variant thereof) may be operably linked to one or more nucleic acid sequences. A promoter may be operably linked to a target. A target may be a gene. A target may be a regulatory RNA (e.g., siRNA, shRNA, miRNA, lncRNA, piRNA, etc.). Examples of targets which may be linked to promoters described herein for use in the disclosed methods include, for example, genes involved in fatty acid synthesis (e.g., FAS1/2, ELO1, ELO2, FAD2, OLE1, SCT1, LSC1, PAH1, DGA1, DGA2, LRO1, etc.), genes involved in lipid breakdown (e.g. peroxisomal enzymes such as PXA1/2, PEX10; fatty acid oxidation genes such as MFE1; lipases such as TGL3, TGL4; etc.), genes involved in fatty acid transport or activation (e.g. ACB1, FAA1-4, etc.), genes involved in diverting carbon flux to undesirable products, genes involved in synthesis or breakdown of glucose, and genes involved in energy metabolism (e.g. phosphoglucose isomerase, phosphofructokinase, ATP citrate lyase, citrate synthase etc.). A target linked to a promoter may be a *Yarrowia lipolytica* gene. Alternatively, a target linked to a promoter may not be a *Yarrowia lipolytica* gene.

A promoter may be linked to a target by introducing the promoter and the target into a nucleic acid molecule, for example, a vector. A vector may be introduced into a cell, thereby expressing the promoter and the target. In one embodiment, a promoter may be linked to a target by introducing a promoter into DNA of a cell, for example, via homologous recombination.

III. Exemplary Nucleic Acids and Methods

Through analysis of publicly available transcriptomic data, transcripts were identified whose abundance dropped at high carbon-to-nitrogen ratios. The promoter regions of these genes were designated as PR104-PR110 (SEQ ID NO:1-7). The inventors took the 1000 bp (or 370 bp for PR108 (SEQ ID NO:5) where the intergenic region is shorter) upstream of the transcription start site of each of the corresponding genes and used them to drive transcription of genes of interest in order to obtain activity during growth but not during lipid accumulation (a transition involving an increase in the carbon-to-nitrogen ratio). In some embodiments, a nucleic acid comprises a nucleotide sequence having at least 70% identity with SEQ ID NO: 1, 2, 5, 6, or 7, or any subsequence or functional variant thereof.

In some embodiments, the nucleic acid comprises a nucleotide sequence having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more sequence identity (or any range derivable therein) with the sequence set forth in SEQ ID NO: 1, 2, 5, 6 or 7. In some embodiments, the nucleic acid comprises a nucleotide sequence that is 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more sequence identity (or any range derivable therein) with the sequence set forth in SEQ ID NO: 1, 2, 5, 6 or 7. In other embodiments, the nucleic acid comprises a nucleotide sequence having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more sequence identity (or any range derivable therein) with a subsequence of SEQ ID NO: 1, 2, 5, 6 or 7. In other embodiments, the nucleic acid comprises a nucleotide sequence having 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more sequence identity (or any range derivable therein) with a subsequence of SEQ ID NO: 1, 2, 5, 6 or 7. In some embodiments, the nucleic acid comprises the nucleotide sequence set forth in SEQ ID NO: 1, 2, 5, 6 or 7. In other embodiments, the nucleic acid comprises a nucleotide sequence consisting of a subsequence of SEQ ID NO: 1, 2, 5, 6 or 7. In certain embodiments, the subsequence retains promoter activity. In certain embodiments, the subsequence retains 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% or 100% (or any range derivable therein) of the promoter activity of the full-length nucleotide sequence. In certain embodiments, the subsequence retains promoter activity. In certain embodiments, the subsequence retains at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% or 100% (or any range derivable therein) of the promoter activity of the full-length nucleotide sequence. In certain embodiments, the subsequence retains the promoter activity of the full-length nucleotide sequence.

In some embodiments, the subsequence is 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, or 300 nucleotides long or longer. In some embodiments, the subsequence comprises 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, or 300 consecutive nucleotides found anywhere in SEQ ID NO: 1, 2, 5, 6 or 7. In some embodiments, the subsequence comprises 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, or 300 consecutive nucleotides at the 3'-terminus of SEQ ID NO: 1, 2, 5, 6 or 7.

In some embodiments, the nucleic acid comprises a nucleotide sequence having or having at least or having at most 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or 100% (or any range derivable therein) sequence identity with 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, or 300 consecutive nucleotides found anywhere in SEQ ID NO: 1, 2, 5, 6 or 7. In some embodiments, the nucleic acid comprises a nucleotide sequence consisting of 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, or 300 consecutive nucleotides found anywhere in SEQ ID NO: 1, 2, 5, 6 or 7. In certain embodiments, the nucleotide sequence retains promoter activity. In certain embodiments, the nucleotide sequence retains at least, at most or retains 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% or 100% (or any percentage derivable therein) of the promoter activity of the full-length nucleotide sequence. In certain embodiments, the nucleotide sequence retains the promoter activity of the full-length nucleotide sequence.

In some embodiments, the nucleic acid comprises a nucleotide sequence having at least or having at most or having 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or 100% (or any percentage derivable therein) sequence identity with 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, or 300 consecutive nucleotides at the 3'-terminus of SEQ ID NO: 1, 2, 5, 6 or 7. In some embodiments, the nucleic acid comprises a nucleotide sequence consisting of 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, or 300 consecutive nucleotides at the 3'-terminus of SEQ ID NO: 1, 2, 5, 6 or 7. In certain embodiments, the nucleotide sequence retains promoter activity. In certain embodiments, the nucleotide sequence retains at least or retains 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% or 100% (or any percentage derivable therein) of the promoter activity of the full-length nucleotide sequence. In certain embodiments, the nucleotide sequence retains the promoter activity of the full-length nucleotide sequence.

Although promoters PR106 (SEQ ID NO: 3) and PR107 (SEQ ID NO: 4) drove very low levels of expression compared to promoters PR104 (SEQ ID NO: 1), PR105 (SEQ ID NO: 2), PR108 (SEQ ID NO: 5), PR109 (SEQ ID NO: 6), and PR110 (SEQ ID NO: 7), in some embodiments, a nucleic acid comprises a nucleotide sequence having at least 70% identity with SEQ ID NO: 3 or 4, or any subsequence or functional variant thereof.

Vectors Comprising Promoters Derived from *Yarrowia lipolytica*

Some embodiments relate to a vector comprising a nucleotide sequence encoding a promoter from *Yarrowia lipolytica*, wherein the promoter is SEQ ID NO:1, 2, 5, 6 or 7, or a subsequence or functional variant thereof. In some embodiments, the vector is a plasmid. In other embodiments, the vector is a linear DNA molecule.

In some embodiments, the nucleotide sequence has or has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or 100% (or any percentage derivable therein) sequence identity with the sequence set forth in SEQ ID NO: 1, 2, 5, 6 or 7. In other embodiments, the nucleotide sequence has or has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or 100% (or any percentage derivable therein) sequence identity with a subsequence of SEQ ID NO: 1, 2, 5, 6 or 7. In some embodiments, the nucleotide sequence comprises the sequence set forth in SEQ ID NO: 1, 2, 5, 6 or 7. In other embodiments, the nucleotide sequence comprises a subsequence of SEQ ID NO: 1, 2, 5, 6 or 7. In certain embodiments, the subsequence retains promoter activity. In certain embodiments, the subsequence retains or retains at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% or 100% (or any percentage derivable therein) of the promoter activity of the full-length nucleotide sequence. In certain embodiments, the subsequence retains the promoter activity of the full-length nucleotide sequence.

In some embodiments, the subsequence is 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, or 300 nucleotides long or longer. In some embodiments, the subsequence comprises 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, or 300 consecutive nucleotides found anywhere in SEQ ID NO: 1, 2, 5, 6 or 7. In some embodiments, the subsequence comprises 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, or 300 consecutive nucleotides at the 3'-terminus of SEQ ID NO: 1, 2, 5, 6 or 7.

In some embodiments, the nucleotide sequence has or has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or 100% (or any percentage derivable therein) sequence identity with 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, or 300 consecutive nucleotides found anywhere in SEQ ID NO: 1, 2, 5, 6 or 7. In some embodiments, the nucleotide sequence comprises 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, or 300 consecutive nucleotides found anywhere in SEQ ID NO: 1, 2, 5, 6 or 7. In certain embodiments, the nucleotide sequence retains promoter activity. In certain embodiments, the nucleotide sequence retains or retains at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% or 100% (or any percentage derivable therein) of the promoter activity of the full-length nucleotide sequence. In certain embodiments, the nucleotide sequence retains the promoter activity of the full-length nucleotide sequence.

In some embodiments, the nucleotide sequence has or has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or 100% (or any percentage derivable therein) sequence identity with 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, or 300 consecutive nucleotides at the 3'-terminus of SEQ ID NO: 1, 2, 5, 6 or 7. In some embodiments, the nucleotide sequence comprises 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, or 300 consecutive nucleotides at the 3'-terminus of SEQ ID NO: 1, 2, 5, 6 or 7. In certain embodiments, the nucleotide sequence retains promoter activity. In certain embodiments, the nucleotide sequence retains or retains at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% (or any percentage derivable therein) of the promoter activity of the full-length nucleotide sequence. In certain embodiments, the nucleotide sequence retains the promoter activity of the full-length nucleotide sequence.

Although promoters PR106 (SEQ ID NO: 3) and PR107 (SEQ ID NO: 4) drove very low levels of expression compared to promoters PR104 (SEQ ID NO: 1), PR105 (SEQ ID NO: 2), PR108 (SEQ ID NO: 5), PR109 (SEQ ID NO: 6), and PR110 (SEQ ID NO: 7), in some embodiments, the nucleotide sequence has at least 70% identity with SEQ ID NO: 3 or 4, or any subsequence or functional variant thereof.

Transformed Cells and Methods of Transforming Cells with Promoters Derived from *Yarrowia lipolytica*

In certain aspects, the disclosure relates to a transformed cell comprising a genetic modification, wherein the genetic modification is transformation with a nucleic acid encoding a promoter from *Yarrowia lipolytica* comprising SEQ ID NO: 1, 2, 5, 6 or 7. In some aspects, the disclosure relates to methods of expressing a gene in a cell comprising transforming a parent cell with a nucleic acid encoding a promoter from *Yarrowia lipolytica*. In some embodiments, the nucleic acid comprises a gene, and the gene and the promoter are operably linked. In other embodiments, the nucleic acid is designed so that the promoter becomes operably linked to a gene after transformation of the parent cell.

In some embodiments, the nucleic acid comprises a nucleotide sequence having or having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more sequence identity (or any percentage derivable therein) with the sequence set forth in SEQ ID NO: 1, 2, 5, 6 or 7. In other embodiments, the nucleic acid comprises a nucleotide sequence having or having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or 100% sequence identity (or any percentage derivable therein) with a subsequence of SEQ ID NO: 1, 2, 5, 6 or 7. In some embodiments, the nucleic acid comprises the nucleotide sequence set forth in SEQ ID NO: 1, 2, 5, 6 or 7. In other embodiments, the nucleic acid comprises a nucleotide sequence consisting of a subsequence of SEQ ID NO: 1, 2, 5, 6 or 7. In certain embodiments, the subsequence retains promoter activity. In certain embodiments, the subsequence retains or retains at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% (or any percentage derivable therein) of the promoter activity of the full-length nucleotide sequence. In certain embodiments, the subsequence retains the promoter activity of the full-length nucleotide sequence.

In some embodiments, the subsequence is 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, or 300 nucleotides long or longer. In some embodiments, the subsequence comprises 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, or 300 consecutive nucleotides found anywhere in SEQ ID NO: 1, 2, 5, 6 or 7. In some embodiments, the subsequence comprises 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, or 300 consecutive nucleotides at the 3'-terminus of SEQ ID NO: 1, 2, 5, 6 or 7.

In some embodiments, the nucleic acid comprises a nucleotide sequence having or having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or 100% (or any percentage derivable therein) sequence identity with 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, or 300 consecutive nucleotides found anywhere in SEQ ID NO: 1, 2, 5, 6 or 7. In some embodiments, the nucleic acid comprises a nucleotide sequence consisting of 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, or 300 consecutive nucleotides found anywhere in SEQ ID NO: 1, 2, 5, 6 or 7. In certain embodiments, the nucleotide sequence retains promoter activity. In certain embodiments, the nucleotide sequence retains or retains at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% or 100% (or any percentage derivable therein) of the promoter activity of the full-length nucleotide sequence. In certain embodiments, the nucleotide sequence retains the promoter activity of the full-length nucleotide sequence.

In some embodiments, the nucleic acid comprises a nucleotide sequence having or having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more (or any percentage derivable therein) sequence identity with 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, or 300 consecutive nucleotides at the 3'-terminus of SEQ ID NO: 1, 2, 5, 6 or 7. In some embodiments, the nucleic acid comprises a nucleotide sequence consisting of 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, or 300 consecutive nucleotides at the 3'-terminus of SEQ ID NO: 1, 2, 5, 6 or 7. In certain embodiments, the nucleotide sequence retains promoter activity. In certain embodiments, the nucleotide sequence retains or retains at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% (or any percentage derivable therein) of the promoter activity of the full-length nucleotide sequence. In certain embodiments, the nucleotide sequence retains the promoter activity of the full-length nucleotide sequence.

Although promoters PR106 (SEQ ID NO: 3) and PR107 (SEQ ID NO: 4) drove very low levels of expression compared to promoters PR104 (SEQ ID NO: 1), PR105 (SEQ ID NO: 2), PR108 (SEQ ID NO: 5), PR109 (SEQ ID NO: 6), and PR110 (SEQ ID NO: 7), in some embodiments, a nucleic acid comprises a nucleotide sequence having at least 70% identity with SEQ ID NO: 3 or 4, or any subsequence or functional variant thereof.

Species of Cells, Parent Cells, and Transformed Host Cells

In some aspects, the current disclosure relates to a host cell comprising any one of SEQ ID NO:1, 2, 5, 6, or 7, or subsequences or variants thereof. The host cell may be selected from the group consisting of algae, bacteria, molds, fungi, plants, and yeasts. In some embodiments, the cell is selected from the group consisting of *Arxula, Aspergillus, Aurantiochytrium, Candida, Claviceps, Cryptococcus, Cunninghamella, Geotrichum, Hansenula, Kluyveromyces, Kodamaea, Leucosporidiella, Lipomyces, Mortierella, Ogataea, Pichia, Prototheca, Rhizopus, Rhodosporidium, Rhodotorula, Saccharomyces, Schizosaccharomyces, Tremella, Trichosporon, Wickerhamomyces,* and *Yarrowia*. In certain embodiments, the cell is selected from the group consisting of *Arxula adeninivorans, Aspergillus niger, Aspergillus orzyae, Aspergillus terreus, Aurantiochytrium limacinum, Candida utilis, Claviceps purpurea, Cryptococcus albidus, Cryptococcus curvatus, Cryptococcus ramirezgomezianus, Cryptococcus terreus, Cryptococcus wieringae, Cunninghamella echinulata, Cunninghamella japonica, Geotrichum fermentans, Hansenula polymorpha, Kluyveromyces lactis, Kluyveromyces marxianus, Kodamaea ohmeri, Leucosporidiella creatinivora, Lipomyces lipofer, Lipomyces starkeyi, Lipomyces tetrasporus, Mortierella isabellina, Mortierella alpina, Ogataea polymorpha, Pichia ciferrii, Pichia guilliermondii, Pichia pastoris, Pichia stipites, Prototheca zopfii, Rhizopus arrhizus, Rhodosporidium babjevae, Rhodosporidium toruloides, Rhodosporidium paludigenum, Rhodotorula glutinis, Rhodotorula mucilaginosa, Saccharomyces cerevisiae, Schizosaccharomyces pombe, Tremella enchepala, Trichosporon cutaneum, Trichosporon fermen-* tans, *Wickerhamomyces ciferrii*, and *Yarrowia lipolytica*. Thus, the cell may be *Yarrowia lipolytica*. The cell may be *Arxula adeninivorans*.

Although promoters PR106 (SEQ ID NO: 3) and PR107 (SEQ ID NO: 4) drove very low levels of expression compared to promoters PR104 (SEQ ID NO: 1), PR105 (SEQ ID NO: 2), PR108 (SEQ ID NO: 5), PR109 (SEQ ID NO: 6), and PR110 (SEQ ID NO: 7), in some embodiments the current disclosure relates to a host cell comprising any one SEQ ID NO: 3 or 4, or subsequences or variants thereof.

Growth of *Y. lipolytica*

The present disclosure also concerns methods for modulating or increasing the lipid content of a transgenic *Yarrowia* species that comprises operably linking a coding sequence to a nucleotide sequence that is at least 80% identical to any of SEQ ID NO:1, 2, 5, 6, or 7, or a variant or subsequence thereof such that the coding sequence has reduced expression in the lipid accumulation phase relative to the growth phase.

The transgenic *Yarrowia* species of the present disclosure can be grown under conditions that produce the greatest and the most economical yield of one or more products of interest (e.g., polyunsaturated fatty acids, lipids, etc.). In general, media conditions may be optimized by modifying the type and amount of carbon source, the type and amount of nitrogen source, the carbon-to-nitrogen ratio, the amount of different mineral ions, the oxygen level, growth temperature, pH, length of the biomass production phase, length of the oil accumulation phase and the time and method of cell harvest. For example, *Yarrowia lipolytica* may be grown in a complex media such as yeast extract-peptone-dextrose broth ["YPD"] or a defined minimal media that lacks a component necessary for growth and thereby forces selection of the desired expression cassettes (e.g., Yeast Nitrogen Base (DIFCO Laboratories, Detroit, Mich.)).

Fermentation media for the methods and host cells described herein must contain a suitable carbon source, such as are described in U.S. Pat. No. 7,238,482 and U.S. Pat. Appl. Publ. No. 2011-0059204-A1. Although it is contemplated that the source of carbon utilized in the present disclosure may encompass a wide variety of carbon-containing sources, preferred carbon sources may include sugars (e.g., glucose, invert sucrose, fructose and combinations of thereof), glycerols and/or fatty acids (e.g., those containing between 10-22 carbons).

Nitrogen may be supplied from an inorganic (e.g., $(NH_4)_2SO_4$) or organic (e.g., urea or glutamate) source. In addition to appropriate carbon and nitrogen sources, the fermentation media must also contain suitable minerals, salts, cofactors, buffers, vitamins and other components known to those skilled in the art suitable for the growth of the recombinant microbial host cell and the promotion of the enzymatic pathways for EPA production. Particular attention is given to several metal ions, such as $Fe^{+2}$, $Cu^{+2}$, $Mn^{+2}$, $Co^{+2}$, $Zn^{+2}$ and $Mg^{+2}$, that promote synthesis of lipids and PUFAs (Nakahara et al., Ind. Appl. Single Cell Oils, D. J. Kyle and R. Colin, eds. pp 61-97 (1992)).

Growth media for the methods and host cells described herein may be common commercially prepared media, such as Yeast Nitrogen Base or corn steep liquors. Other defined or synthetic growth media may also be used. A suitable pH range for the fermentation is typically between about pH 4.0 to pH 8.0, wherein pH 5.5 to pH 7.5 is preferred as the range for the initial growth conditions. The fermentation may be conducted under aerobic or anaerobic conditions, wherein microaerobic conditions are preferred.

U.S. Pat. Appl. Publ. No. 2009-0093543-A1 provides a detailed description of parameters required for a 2-L fermentation of the recombinant *Yarrowia lipolytica* strain Y4305 (whose maximum production was 12.1 EPA % DCW [55.6 EPA % TFAs, with a ratio of EPA % TFAs to LA % TFAs of 3.03] over a period of 162 hours). This disclosure includes a description of means to prepare inocula from frozen cultures to generate a seed culture, initially culture the yeast under conditions that promoted rapid growth to a high cell density, and then culture the yeast to promote lipid and PUFA accumulation (via starving for nitrogen and continuously feeding glucose). Process variables including temperature (controlled between 30-32° C.), pH (controlled between 5-7), dissolved oxygen concentration and glucose concentration were monitored and controlled per standard operating conditions. Additional example methods for culturing *Yarrowia lipolytica* for lipid accumulation are described in Friedlander et al., Biotechnology for Biofuels, 9:77, (2016).

Modified Promoter Regions

Some embodiments are directed to wildtype *Yarrowia* promoter regions of SEQ ID NO:1, 2, 6, or 7. Some embodiments are directed to a modified *Yarrowia* promoter region relative to SEQ ID NO:1, 2, 6, or 7. A modified *Yarrowia* promoter region may comprise the promoter region wherein the promoter optionally comprises at least one modification selected from the group consisting of: a) a deletion at the 5'-terminus of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634 or 635 consecutive nucleotides; and b) a deletion at the 3'-terminus of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634 or 635 consecutive nucleotides. A modified *Yarrowia* promoter region may comprise both a deletion from the 5' terminus and a deletion from the 3' terminus. A modified *Yarrowia* promoter region disclosed herein, in some embodiments, comprises any contiguous region of SEQ ID NO: 1, 2, 6, or 7 capable of acting as a promoter.

Similarly, a modified *Yarrowia* promoter region may comprise the promoter region of SEQ ID NO: 5, wherein the promoter optionally comprises at least one modification selected from the group consisting of: a) a deletion at the 5'-terminus of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, or 200 consecutive nucleotides; and b) a deletion at the 3'-terminus of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, or 200 consecutive nucleotides. A modified *Yarrowia* promoter region may comprise both a deletion from the 5' terminus and a deletion from the 3' terminus. A modified *Yarrowia* promoter region disclosed herein, in some embodiments, comprises any contiguous region of SEQ ID NO: 5 capable of acting as a promoter.

IV. Examples

The following examples are included to demonstrate certain embodiments of the disclosure. It should be appreciated by those of skill in the art that the techniques disclosed in the examples which follow represent techniques discovered by the inventor to function well in the practice of the disclosure. However, those of skill in the art should, in light of the present disclosure, appreciate that many changes can be made in the specific embodiments which are disclosed and still obtain a like or similar result without departing from the spirit and scope of the disclosure. The Examples should not be construed as limiting in any way. The contents of all cited references (including literature references, issued patents, published patent applications, and GenBank Accession numbers as cited throughout this application) are hereby expressly incorporated by reference. When definitions of terms in documents that are incorporated by reference herein conflict with those used herein, the definitions used herein govern.

Example 1

A. Driving Delta-12 Fatty Acid Desaturase (FAD2) with Promoters PR104-PR110 in a Δfad2 Strain In *Y. lipolytica*, delta-12 fatty acid desaturase enzyme (FAD2, YALIOB10153) is known to act on oleate (C18:1)

and add a double bond in the Δ12 position to produce linoleate (C18:2). This conversion occurs in the phospholipid species of oleate and linoleate is naturally produced during growth. When wild-type cells enter lipid accumulation which involves increased fatty acyl-CoA storage into triacylglycerides (TAGs), there is a natural dilution effect of linoleate in the total fraction of fatty acids, although a significant amount of linoleate is still stored as TAGs (FIGS. 8A and B, compare YB-392 16 h and 96 h).

To characterize the promoters in this study, FAD2 was expressed and driven by PR104-PR110 in a Δ12 desaturase null strain. The endogenous FAD2 was deleted by targeted integration in wild-type strain YB-392 to create strain NS419. Tsakraklides et al. demonstrated that deleting this gene leads to elimination of all detectable linoleate and a concomitant increase in oleate (Tsakraklides et al., Biotechnology for Biofuels, 2018). The Δfad2 strain NS419 was transformed with cassettes driving expression of FAD2 from each promoter. All characterizations of the strains were performed in batch fermentation for 96 hours in lipid production media (C:N~86). These conditions allow for growth during the first day while nitrogen is available to produce biomass and lipid accumulates through the next three days when nitrogen is depleted. Analyses of the cells included gas chromatography (GC) for measuring the lipid composition, qPCR and microscopic imaging. NS419 (Δfad2) and YB-392 (wild-type) were included as controls. 12 transformants were chosen per promoter transformation and grown in 96-deep well plates. Cell pellets were analyzed by GC for lipid composition at day 1 and day 4. Two transformants which represented the average performance of the 12 transformants were chosen to be re-analyzed in 24 well plates. From the 24-well plates, one strain from each set was chosen to be tested in shake flasks along with the control strains NS419 (Δfad2) and YB-392.

Figure 8B:
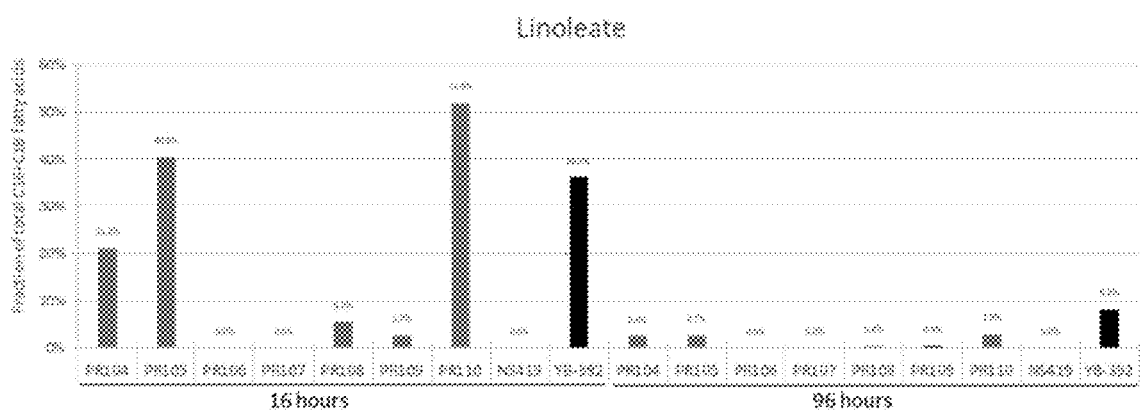
Figure 8C:
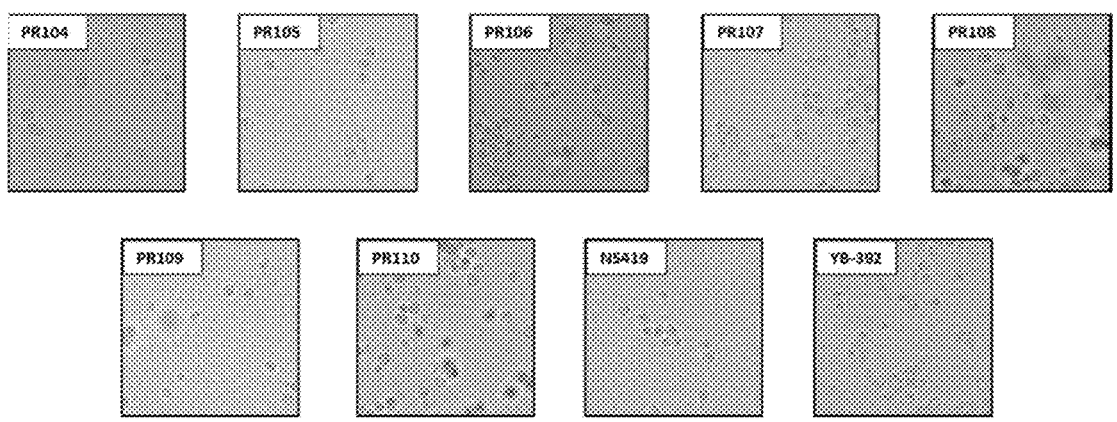

Shake flask culture samples were taken at 16 h and 96 h and relative fatty acid composition was determined (FIGS. 8A and 8B). As the Δfad2 parent strain NS419 cannot produce linoleate, the levels of linoleate in the transformed strains can be interpreted as an indication of Δ12 desaturase levels and therefore promoter activity in driving FAD2 transcription. Based on the percent linoleate present at 16 h (FIG. 8B), transformants with PR110-FAD2, PR105-FAD2 and PR104-FAD2 were the highest expressors of FAD2 in the growth phase, followed by PR108-FAD2, PR109-FAD2 and finally, PR106-FAD2 and PR107-FAD2 which were similar to NS419 (showing almost no activity during growth and lipid phase). By 96 h, all the transformants record linoleate fractions lower than YB-392 (wild type strain), even in the case of PR105 and PR110 that contained higher linoleate fractions than YB-392 at 16 h. Microscopic observation of the transformants and the control strains at 96 h (FIG. 8C) reveals no discernible defects in growth or lipid production and all strains appear similar to the control strains.

The same samples were analyzed by qPCR to characterize promoter activity and relate transcription to lipid composition (Table 2). The promoter with the highest FAD2 transcript levels at 16 h (PR110) recorded the highest percent linoleate, while the promoters with the lowest recorded (PR107) or undetectable FAD2 mRNA levels (PR106 and NS419) had no measurable linoleate (Table 2, column B and FIG. 8B). To compare promoter activity between growth and lipid accumulation, the ratio of transcript levels and the ratio of linoleate levels at 16 h over 96 h were calculated (Table 2). FAD2 expression from the native promoter was relatively stable between 16 h and 96 h but linoleate content dropped 4.5-fold during lipid accumulation in the wild-type strain as fatty acids were directed to TAG storage. Promoters PR105, 108, 109 and 110 show repression ranging from 2.6- to >1800-fold between growth and lipid accumulation (Table 2). This transcriptional repression correlates with the sharper decrease of percent linoleate for these four promoters between the two time points (ranging from 6- to 18-fold) when compared to YB-392 (FIG. 8B). Note that all strains attained similar accumulation of lipid (FIG. 8C), suggesting that, despite the dilution effect caused by lipid production, FAD2 repression in PR105-110 strains further diminished desaturase activity which was reflected in the lower linoleate composition measured. The relative weakness of promoters PR104, PR108 and PR109 in comparison to the native promoter during growth led to lower-than-wild-type linoleate levels at 16 h (Table 2 and FIG. 8B) and contributed to the low linoleate levels during lipid accumulation

TABLE 2

FAD2 transcript levels of transformants and control strains measured by qPCR. All calculations were carried out using 2-ΔΔCt method (24).

| Strain | FAD2 transcript relative to YB-392 at 16 h | FAD2 transcript relative to YB-392 at 96 h | Ratio (FAD2 transcript at 16 h/96 h) | Ratio (linoleate at 16 h/96 h) |
|---|---|---|---|---|
| PR104 | 13% | 15% | 0.9 | 8 |
| PR105 | 109% | 0.7% | 178 | 15 |
| PR106 | N/A | N/A | N/A | ND |
| PR107 | 0.25% | 0.9% | 0.3 | ND |
| PR108 | 14% | 1.7% | 8.8 | 14 |
| PR109 | 7.4% | 3% | 2.6 | 7 |
| PR110 | 231% | 0.14% | 1855 | 18 |
| NS419 (Δfad2) | N/A | N/A | N/A | N/A |
| YB-392 (wt) | 100% | 100% | 1.1 | 4.5 |

N/A refers to quantities that were too low for detection by qPCR.

B. Driving Delta-9 Fatty Acid Desaturase (OLE1) with Promoters PR104-PR110 in a Δole1 Strain

*Y. lipolytica* Δ9 desaturase (OLE1, YALI0C05951) acts on saturated fatty acids palmitic acid (C16:0) and stearic acid (C18:0) to produce the corresponding unsaturated fatty acids palmitoleic acid (C16:1) and oleic acid (C18:1). Deletion of the *Y. lipolytica* Δ9 desaturase OLE1 causes auxotrophy for monounsaturated fatty acids and reintroduction of an active Δ9 desaturase rescues growth on unsupplemented media.

Similar to the above experiment, a desaturase null strain was used. OLE1 was deleted by targeted integration in wild-type strain YB-392 to create strain NS418. NS418 was cultured in media supplemented with monounsaturated fatty acids to maintain viability and transformed with expression cassettes for containing OLE1 driven by PR104-110. Transformants were selected through antibiotic resistance on supplemented plates and then tested for their ability to rescue growth on unsupplemented media. Promoters PR104, PR105, PR109 and PR110 enabled growth on media without supplementation, indicating that sufficient Δ9 desaturase activity was produced during growth phase to supply essential monounsaturated fatty acids. PR106-PR108 strains, similar to the parent Δole1 strain NS418, could not grow without supplementation suggesting that OLE1 expression was below levels necessary for growth. These strains were therefore excluded from subsequent analysis as they cannot grow in the lipid production media which does not contain monounsaturated fatty acids.

Figure 9A:
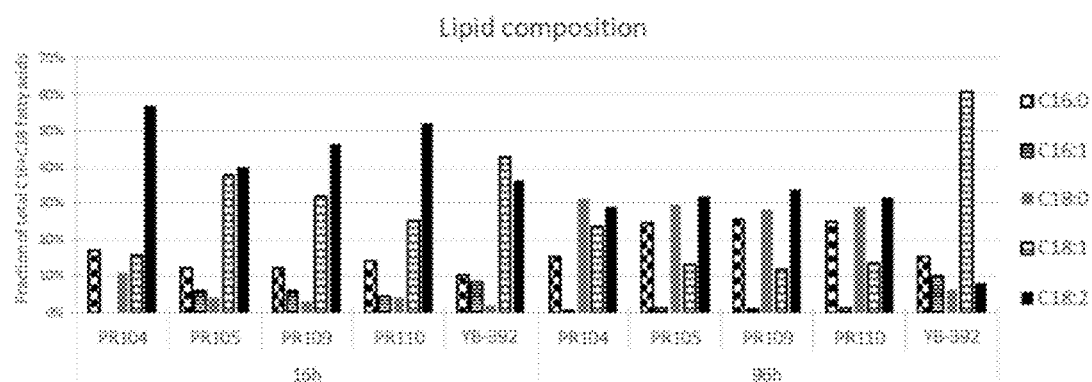
FIGS. 9A-9C show results from experiments described in Example 1.
Figure 9B:
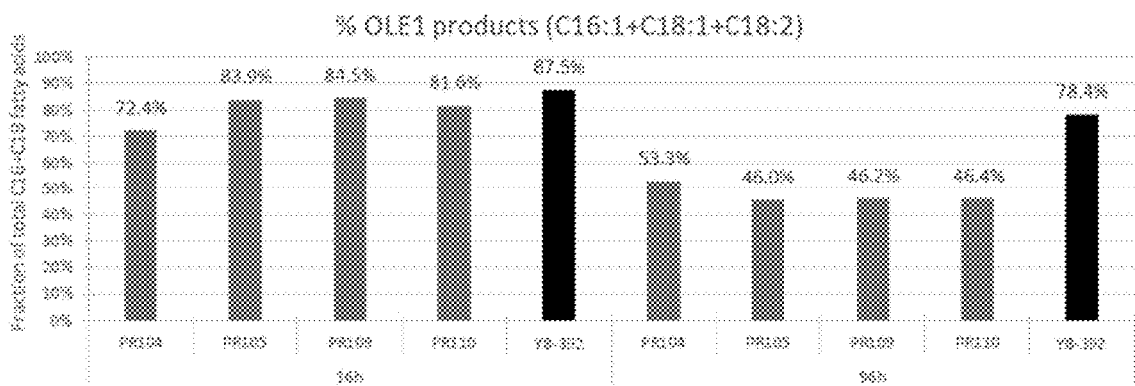
Figure 9C:
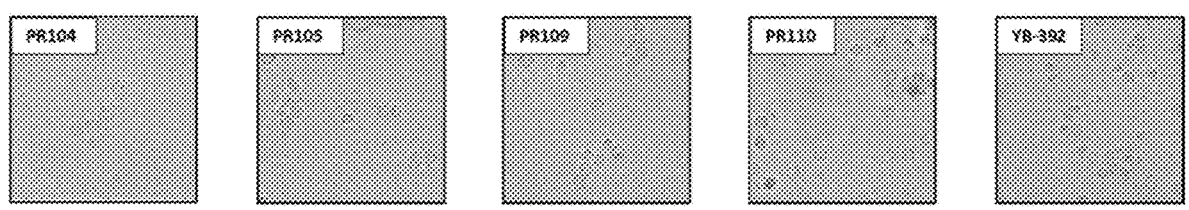

Representative transformants of PR104, PR105, PR109, PR110-OLE1 and YB-392 were sampled, and analyzed as for the FAD2 experiment. Composition measurements (FIG. 9A) revealed varying lipid profiles for PR104, PR105, PR109 and PR110 transformants compared to each other and compared to wild type strain. To better understand the OLE1 expression effect, the direct (C16:1, C18:1) and indirect products (C18:2, made from C18:1) of Δ9 desaturase were combined and reported in FIG. 9B. The reduction of Δ9 desaturated fatty acids by 96 h compared to the wild type strain suggests reduced OLE1 activity after growth. Microscopic observation of the transformants at 96 h reveal very small lipid bodies when compared to YB-392 (FIG. 9C). OLE1 is known to be an important gene in the lipid production pathway. Low OLE1 levels during the lipid accumulation phase may result in strains unable to accumulate lipids and therefore producing smaller lipid bodies.

qPCR measurements showed that all four promoters produce lower transcript levels at 16 h than the native promoter (Table 3). This result agreed with the lower fraction of Δ9 desaturated fatty acids measured at this time point (FIG. 9B). In the wild-type strain, both OLE1 transcript levels and Δ9 desaturated fatty acid levels were slightly reduced at 96 h. OLE1 transcript levels for promoters PR105, PR109 and PR110 at 96 h were greatly reduced compared to 16 h values and compared to YB-392. This result was also in agreement with GC composition data which showed lower Δ9 desaturated fatty acids for these strains at 96 h than 16 h and also a greater reduction of D9 desaturated fatty acids between the time points than YB-392 (FIG. 9B and Table 3). The very low OLE1 transcript levels measured at 96 h for PR105, PR109 and PR110 strains is also responsible for the small size of lipid bodies observed in these cells (FIG. 9C).

TABLE 3

OLE1 transcript levels of transformants and control strain measured by qPCR. All calculations were carried out using 2-ΔΔCt method.

| Strain | OLE1 transcript relative to YB-392 at 16 h | OLE1 transcript relative to YB-392 at 96 h | ratio: OLE1 transcript at 16 h/96 h | ratio: Δ9 products at 16 h/96 h |
|---|---|---|---|---|
| PR104 | 9.8% | 11% | 1 | 1.4 |
| PR105 | 23% | 0.44% | 63 | 1.8 |
| PR109 | 20% | 0.39% | 63 | 1.8 |
| PR110 | 38% | 0.07% | 688 | 1.8 |
| YB-392 (wt) | 100% | 100% | 1.2 | 1.1 |

C. Methods

1. Strains and Media

Wild-type *Yarrowia lipolytica* strain YB-392 was obtained from the ARS Culture Collection (NRRL). All strains were cultured in YPD (10 g/L yeast extract, 20 g/L bacto peptone, and 20 g/L glucose) at 30° C. 20 g/L agar was added to prepare solid media. Antibiotic selection was achieved with the addition of hygromycin B (300 μg/mL) or nourseothricin (500 μg/mL) as appropriate. The lipid production media containing 0.5 g/L urea, 1.5 g/L yeast extract, 0.85 g/L casamino acids, 1.7 g/L YNB (without amino acids and ammonium sulfate), 100 g/L glucose, and 5.11 g/L potassium hydrogen phthalate (25 mM) was used for characterizing strains in plates and flasks. 1.5 mL of media was used per well for 24-well plates and 300 μl of media was used per well for 96-well plates. Alternatively, the yeast cultures were used to inoculate 50 ml of sterilized media in an autoclaved 250 mL flask. Yeast strains that had been incubated for 1-2 days on YPD-agar plates at 30° C. were used to inoculate each well of the multiwell plate.

2. Fatty Acid Composition Measurement

To obtain a lipid composition profile, a plate transesterification procedure was developed to extract and convert lipids to FAMEs. Samples from shake flasks were pipetted into the wells of a 96-well plate and after pelleting by centrifugation, cells were washed with water. Fluffy pellets were made by vortexing the washed cells with a small amount of water and freezing at −80° C. for 30 min before placing the entire plate in a lyophilizer overnight. To each well 500 μL 1.25 M HCl in Methanol (Sigma®) was added and the plate was sealed closed and incubated at 85° C. for 1.5 h with mixing by pipetting at 30-min intervals. 1 mL isooctane and 0.5 mL water were then added to each well and mixed by vortexing. A sample of the FAME-containing isooctane layer was analyzed by gas chromatography and composition was determined as percent of total peak area (sum of C16:0, C16:1, C18:0, C18:1, and C18:2) for each FAME species. Because the dry cell weight in each of the 96 wells is not measured, this method yields relative compositional analysis by comparing peak areas within each sample and not quantitative fatty acid levels. For samples from shake flasks, 1 ml sample was pelleted, washed with water and frozen at −80° C. for 30 min and extraction and GC analysis was carried out in a similar manner as described above.

3. Targeted Deletions

Targeted genomic integrations to construct background strains NS418 and NS419 are previously described (Tsakraklides et al., Biotechnology for Biofuels, 2018). To delete *Y. lipolytica* genes OLE1 and FAD2 and to construct strains NS418 and NS419 respectively, the hygromycin selectable marker gene was amplified by PCR using oligonucleotide primers that attach short flanks homologous to the promoter and terminator of target genes immediately 5' and 3' to the ORF in combination with internal marker gene primers. A two-fragment deletion cassette was thus made for each target such that the fragments overlapped in the marker reading frame, but neither fragment alone contained the entire functional antibiotic-resistance gene. PCR products were transformed into hydroxyurea (Sigma-Aldrich®)-treated cells.

4. Gene Overexpression

Using standard molecular biology techniques, linear expression constructs were prepared. Each expression construct contained an expression cassette for the gene of interest (OLE1 or FAD2) driven by the promoters (PR104-PR110) described in this study, in tandem with an expression cassette for the nourseothricin selectable marker. These constructs were transformed into corresponding deletion mutant *Y. lipolytica* strains (Δole1 or Δfad2) leading to random integration into the genome which can lead to expression differences. 10-12 transformants selected on YPD/nourseothricin plates were grown in lipid production media for 96 h in 96-deep well plates and the cell pellets were analyzed by Gas Chromatography. From this screen, two average transformants were chosen for a similar analysis in 24-well plates and finally one of those transformants was chosen to be tested in shake flasks. The cells from shake flasks were tested for lipid composition and transcript levels by qPCR.

5. Transformation

For targeted integrations to delete endogenous genes FAD2 and OLE1, log-phase *Y. lipolytica* cells were treated with 50 mM hydroxyurea for 2 h (targeted integration). For overexpression of FAD2 and OLE1 genes driven by promoters PR104-110, *Y. lipolytica* cells were processed directly for transformation (random integration). Cells were washed with water and resuspended in a volume of water equal to the wet cell pellet. 50 µL was aliquoted per transformation reaction. 18 µL of desired DNA and 92 µL of transformation mix (80 µL 60% PEG4000, 5 µL 2 M DTT, 5 µL 2 M lithium acetate pH 6, and 2 µL 10 mg/mL single stranded salmon sperm DNA) were added to the cell pellet. The transformation reaction was mixed by vortexing and heat shocked at 39° C. for 1 h. Cells were centrifuged, the supernatant was discarded, and cells were resuspended in 1 mL of a suitable non-selective medium like YPD, transferred to culture tubes, and cultured overnight at 30° C. before plating 100 µl (random integration) or all the cells (targeted integration) on selective media.

6. RNA Extraction and Transcript Quantification

Shake flask cultures grown in lipid production media were sampled at 16 h and 96 h at an OD600 of 20 and the cell pellets were stored at −80° C. Total RNA was extracted using TRIzol™ reagent (Invitrogen®, cat. no. 15596026, Pub. no. MAN0001271). Genomic DNA was removed using DNase (Qiagen®, Qiagen, cat no. 79254) followed by RNA cleanup using the Qiagen RNeasy Mini Kit (Cat.no. 74134). 500 ng of clean RNA was used for cDNA synthesis using M-MuLV Reverse Transcriptase enzyme (NEB®, Cat No. M0253S). PCR quantification was done using PerfeCTa® SYBR® qPCR mix with High ROX as a reference dye by QuantaBio (Cat.No. 95055). The reactions were run in PCR-96-LP-AB-C plates by Corning on the Applied Biosystems' StepOnePlus. Software analysis was performed with Applied Biosystems® StepOne v.2.3 software. YlACT1 encoding for actin was used as a reference gene and gene expression levels were standardized using actin gene as the reference (ΔCT method). For comparisons to YB-392 at 16 h and 96 h, the 2-ΔΔCT method was used to calculate fold difference and then converted to percent change. The 2-ΔΔCT method was also used for measuring fold repression for each strain, between the 16 h time point and 96 h time point. The qPCR primers are listed in Table 4.

TABLE 4

List of qPCR primers

| Primer | Sequence |
| --- | --- |
| OLE1 qPCR_F | CACAACCTGCTTGCCACCATG |
| OLE1 qPCR_R | CAGCTCGGTGGATTCGGTTTC |
| FAD2 qPCR_F | CCATGACATCATCGAGACCCACG |
| FAD2 qPCR_R | GTTGGTGTCGTCGTGTCGGTAG |
| ACT1 qPCR_F | GCTGCTGGTATCCACGAGACTAC |
| ACT1 qPCR_R | GCGGAGATCTCCTTGTGCATTCG |

All of the methods disclosed and claimed herein can be made and executed without undue experimentation in light of the present disclosure. While the compositions and methods of this disclosure have been described in terms of preferred embodiments, it will be apparent to those of skill in the art that variations may be applied to the methods and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

The references recited in the application, to the extent that they provide exemplary procedural or other details supplementary to those set forth herein, are specifically incorporated herein by reference.

REFERENCES

The following references and the publications referred to throughout the specification, to the extent that they provide exemplary procedural or other details supplementary to those set forth herein, are specifically incorporated herein by reference.

Nicaud J-M. *Yarrowia lipolytica.* Yeast. 2012 October; 29(10):409-18.

Thevenieau F, Nicaud J-M, Gaillardin C. Applications of the Non-Conventional Yeast *Yarrowia lipolytica.* In: Satyanarayana T, Kunze G, editors. Yeast Biotechnology: Diversity and Applications [Internet]. Dordrecht: Springer Netherlands; 2009 [cited 2019 Apr. 3]. p. 589-613. Available on the world wide web at link.springer-.com/10.1007/978-1-4020-8292-4_26

Blanchin-Roland S, Cordero Otero R R, Gaillardin C. Two upstream activation sequences control the expression of the XPR2 gene in the yeast *Yarrowia lipolytica.* Molecular and Cellular Biology. 1994 January; 14(1):327-38.

Müller S, Sandal T, Kamp-Hansen P, Dalbøge H. Comparison of expression systems in the yeasts *Saccharomyces cerevisiae, Hansenula polymorpha, Klyveromyces lactis, Schizosaccharomyces pombe* and *Yarrowia lipolytica.* Cloning of two novel promoters from *Yarrowia lipolytica.* Yeast. 1998 October; 14(14):1267-83.

Juretzek T, Wang H-J, Nicaud J-M, Mauersberger S, Barth G. Comparison of Promoters Suitable for Regulated Overexpression of β-Galactosidase in the Alkane-Utilizing Yeast *Yarrowia lipolytica.* Biotechnol Bioprocess Eng. 2000; 5(5):7.

Trassaert M, Vandermies M, Carly F, Denies O, Thomas S, Fickers P, et al. New inducible promoter for gene expression and synthetic biology in *Yarrowia lipolytica.* Microbial Cell Factories [Internet]. 2017 December [cited 2018 Jun. 17]; 16(1). Available on the world wide web at microbialcellfactories.biomedcentral.com/articles/10.1186/s12934-017-0755-0

Madzak C, Tréton B, Blanchin-Roland S. Strong Hybrid Promoters and Integrative Expression/Secretion Vectors for Quasi-Constitutive Expression of Heterologous Proteins in the Yeast *Yarrowia lipolytica.*:10.

Blazeck J, Liu L, Redden H, Alper H. Tuning Gene Expression in *Yarrowia lipolytica* by a Hybrid Promoter Approach. Applied and Environmental Microbiology. 2011 Nov. 15; 77(22):7905-14.

Blazeck J, Reed B, Garg R, Gerstner R, Pan A, Agarwala V, et al. Generalizing a hybrid synthetic promoter approach in *Yarrowia lipolytica.* Applied Microbiology and Biotechnology. 2013 April; 97(7):3037-52.

Shabbir Hussain M, Gambill L, Smith S, Blenner M A. Engineering Promoter Architecture in Oleaginous Yeast *Yarrowia lipolytica.* ACS Synthetic Biology. 2016 Mar. 18; 5(3):213-23.

Madzak C. *Yarrowia lipolytica*: recent achievements in heterologous protein expression and pathway engineering. Applied Microbiology and Biotechnology. 2015 June; 99(11):4559-77.

Larroude M, Rossignol T, Nicaud J-M, Ledesma-Amaro R. Synthetic biology tools for engineering *Yarrowia lipolytica*. Biotechnology Advances. 2018 Dec. 1; 36(8): 2150-64.

Hong S-P, Seip J, Walters-Pollak D, Rupert R, Jackson R, Xue Z, et al. Engineering *Yarrowia lipolytica* to express secretory invertase with strong FBA1IN promoter: Secretory invertase expression with FBA1IN promoter from *Y. lipolytica*. Yeast. 2012 February; 29(2):59-72.

Xue Z, Sharpe P L, Hong S-P, Yadav N S, Xie D, Short D R, et al. Production of omega-3 eicosapentaenoic acid by metabolic engineering of *Yarrowia lipolytica*. Nature Biotechnology. 2013 August; 31(8):734-40.

Wong L, Engel J, Jin E, Holdridge B, Xu P. YaliBricks, a versatile genetic toolkit for streamlined and rapid pathway engineering in *Yarrowia lipolytica*. Metabolic Engineering Communications. 2017 Dec. 1; 5:68-77.

Ogrydziak D M, Scharf S J. Alkaline Extracellular Protease Produced by *Saccharomycopsis lipolytica* CX161-1B. Microbiology. 1982; 128(6):1225-34.

Sassi H, Delvigne F, Kar T, Nicaud J-M, Coq A-MC-L, Steels S, et al. Deciphering how LIP2 and POX2 promoters can optimally regulate recombinant protein production in the yeast *Yarrowia lipolytica*. Microbial Cell Factories [Internet]. 2016 December [cited 2018 Jun. 17]; 15(1). Available on the world wide web at microbialcellfactories.biomedcentral.com/articles/10.1186/s12934-016-0558-8

Xue Z, Zhu Q. Ammonium transporter promoter for gene expression in oleaginous yeast [Internet]. US20060094102A1, 2006

Beopoulos A, Cescut J, Haddouche R, Uribelarrea J-L, Molina-Jouve C, Nicaud J-M. *Yarrowia lipolytica* as a model for bio-oil production. Progress in Lipid Research. 2009 November; 48(6):375-87.

Abghari A, Madzak C, Chen S. Combinatorial Engineering of *Yarrowia lipolytica* as a Promising Cell Biorefinery Platform for the de novo Production of Multi-Purpose Long Chain Dicarboxylic Acids. Fermentation. 2017 Aug. 18; 3(3):40.

Abidi S H I, Yang W-C, Watson N, Kumaran P. Engineering Lipid Overproduction in Heterotrophic Microbes.:37.

E-GEOD-35445<Browse<ArrayExpress<EMBL-EBI [Internet]. [cited 2019 Apr. 21]. Available on the world wide web at ebi.ac.uk/arrayexpress/experiments/E-GEOD-35445/

Tsakraklides V, Kamineni A, Consiglio A L, MacEwen K, Friedlander J, Blitzblau H G, et al. High-oleate yeast oil without polyunsaturated fatty acids. Biotechnology for Biofuels [Internet]. 2018 December [cited 2018 Jun. 17]; 11(1). Available on the world wide web at biotechnologyforbiofuels.biomedcentral.com/articles/10.1186/s13068-018-1131-y Livak K J, Schmittgen T D. Analysis of Relative Gene Expression Data Using Real-Time Quantitative PCR and the $2^{-\Delta\Delta C_T}$ Method. Methods. 2001 Dec. 1; 25(4):402-8.

Dobrzyn A, Ntambi J M. The role of stearoyl-CoA desaturase in the control of metabolism. Prostaglandins Leukot Essent Fatty Acids. 2005 July; 73(1):35-41.

Friedlander J, Tsakraklides V, Kamineni A, Greenhagen E H, Consiglio A L, MacEwen K, et al. Engineering of a high lipid producing *Yarrowia lipolytica* strain. Biotechnology for Biofuels [Internet]. 2016 December [cited 2018 Jun. 17]; 9(1). Available on the world wide web at biotechnologyforbiofuels.biomedcentral.com/articles/10.1186/s13068-016-0492-3

Tsakraklides V, Brevnova E, Stephanopoulos G, Shaw A J. Improved Gene Targeting through Cell Cycle Synchronization. Galli A, editor. PLOS ONE. 2015 Jul. 20; 10(7): e0133434.

Chen D-C, Beckerich J-M, Gaillardin C. One-step transformation of the dimorphic yeast *Yarrowia lipolytica*. Appl Microbiol Biotechnol. 1997 Aug. 1; 48(2):232-5.

---

What is claimed is:

1. A nucleic acid molecule comprising:
   a first sequence having at least 80% sequence identity to SEQ ID NO:1, 2, 5, 6 or 7, wherein the first sequence has promoter activity in a yeast cell; and
   a second sequence operably linked to the first sequence, wherein the second sequence is heterologous to the first sequence, and wherein the second sequence comprises a coding sequence.

2. A yeast cell comprising the nucleic acid molecule of claim 1.

3. The yeast cell of claim 2, wherein the yeast cell is an *Arxula adeninivorans, Candida utilis, Hansenula polymorpha, Kluyveromyces lactis, Kluyveromyces marxianus, Kodamaea ohmeri, Lipomyces lipofer, Lipomyces starkeyi, Lipomyces tetrasporus, Ogataea polymorpha, Pichia ciferrii, Pichia guilliermondii, Pichia pastoris, Pichia stipites, Rhodosporidium babjevae, Rhodosporidium toruloides, Rhodosporidium paludigenum, Rhodotorula glutinis, Rhodotorula mucilaginosa, Saccharomyces cerevisiae, Schizosaccharomyces pombe, Wickerhamomyces ciferrii* or *Yarrowia lipolytica* cell.

4. The yeast cell of claim 3, wherein the yeast cell is a *Yarrowia lipolytica*.

5. A method comprising culturing the yeast cell of claim 2 under conditions sufficient to express the coding sequence.

6. The method of claim 5, wherein the cell is cultured for at least 10 passages.

7. The method of claim 5, wherein the coding sequence comprises SCT1.

8. The method of claim 5, wherein yeast cell is a *Yarrowia lipolytica*.

9. The nucleic acid molecule of claim 1, wherein the first sequence comprises SEQ ID NO:1, 2, 5, 6 or 7.

10. The nucleic acid molecule of claim 1, wherein the second sequence is not from *Yarrowia lipolytica*.

11. The nucleic acid molecule of claim 1, wherein the second sequence comprises SCT1.

12. The nucleic acid molecule of claim 1, wherein the first sequence is a subsequence of SEQ ID NO:1, 2, 5, 6 or 7.

13. The nucleic acid molecule of claim 1, wherein the first sequence is capable of inducing increased expression of the second sequence in a growth phase of a yeast cell relative to a lipid accumulation phase of the yeast cell.

14. The nucleic acid molecule of claim 1, wherein the first sequence has at least 85% sequence identity to SEQ ID NO:1, 2, 5, 6 or 7.

15. The nucleic acid molecule of claim 1, wherein the first sequence has at least 90% sequence identity to SEQ ID NO:1, 2, 5, 6 or 7.

16. The nucleic acid molecule of claim 1, wherein the first sequence has at least 95% sequence identity to SEQ ID NO:1, 2, 5, 6 or 7.

17. The nucleic acid molecule of claim 1, wherein the yeast cell is a *Yarrowia lipolytica*.

18. A method of optimizing lipid production of a cell during a fermentation process, wherein the fermentation process comprises a growth phase and a lipid accumulation phase, the method comprising:
   (a) introducing into a cell a nucleic acid molecule comprising a promoter sequence having at least 80% sequence identity to SEQ IQ NO: 1, 2, 5, 6, or 7 to obtain a recombinant cell comprising the promoter sequence operably linked to a coding sequence, wherein the coding sequence is heterologous to the promoter sequence; and
   (b) culturing the recombinant cell.

19. The method of claim 18, wherein the coding sequence comprises SCT1.

20. A method of regulating the expression or activity of a coding sequence during a fermentation process wherein the fermentation process comprises a growth phase and a lipid accumulation phase, the method comprising:
   (a) introducing a nucleic acid molecule into a yeast cell, wherein the nucleic acid molecule comprises the coding sequence operably linked to a promoter sequence, wherein the coding sequence is heterologous to the promoter sequence, and wherein the promoter sequence has at least 80% sequence identity to SEQ ID NO: 1, 2, 5, 6, or 7; and
   (b) culturing the cell, thereby regulating expression or activity of the coding sequence.

21. The method of claim 20, wherein the expression or activity of the coding sequence during the lipid accumulation phase is reduced by at least 90% as compared to the growth phase.

22. The method of claim 20, wherein the cell is selected from the group consisting of *Arxula adeninivorans, Candida utilis, Hansenula polymorpha, Kluyveromyces lactis, Kluyveromyces marxianus, Kodamaea ohmeri, Lipomyces hpofer, Lipomyces starkeyi, Lipomyces tetrasporus, Ogataea polymorpha, Pichia ciferrii, Pichia guilliermondii, Pichia pastoris, Pichia stipites, Rhodosporidium babjevae, Rhodosporidium toruloides, Rhodosporidium paludigenum, Rhodotorula glutinis, Rhodotorula mucilaginosa, Saccharomyces cerevisiae, Schizosaccharomyces pombe, Wickerhamomyces ciferrii*, and *Yarrowia lipolytica*.

\* \* \* \* \*

UNITED STATES PATENT AND TRADEMARK OFFICE
CERTIFICATE OF CORRECTION

PATENT NO. : 11,572,546 B2
APPLICATION NO. : 16/942509
DATED : February 7, 2023
INVENTOR(S) : Vasiliki Tsakraklides et al.

It is certified that error appears in the above-identified patent and that said Letters Patent is hereby corrected as shown below:

In the Claims

In Claim 22, Column 24, Line 50, delete "*hpofer*" and insert --*lipofer*-- therefor.

Signed and Sealed this
Twenty-first Day of March, 2023

Katherine Kelly Vidal
*Director of the United States Patent and Trademark Office*